United States Patent
Bhavnagri

(10) Patent No.: US 11,798,657 B2
(45) Date of Patent: Oct. 24, 2023

(54) SYSTEM AND METHOD FOR CREATING LEAD COMPOUNDS, AND COMPOSITIONS THEREOF

(71) Applicant: Burzin Bhavnagri, Lysterfield (AU)

(72) Inventor: Burzin Bhavnagri, Lysterfield (AU)

(*) Notice: Subject to any disclaimer, the term of this patent is extended or adjusted under 35 U.S.C. 154(b) by 1042 days.

(21) Appl. No.: 16/572,482

(22) Filed: Sep. 16, 2019

(65) Prior Publication Data

US 2021/0082542 A1 Mar. 18, 2021

(51) Int. Cl.
| | |
|---|---|
| *G16C 20/50* | (2019.01) |
| *G16C 20/40* | (2019.01) |
| *G06N 5/01* | (2023.01) |
| *G06F 16/2458* | (2019.01) |
| *G06F 16/901* | (2019.01) |

(52) U.S. Cl.
CPC ......... *G16C 20/50* (2019.02); *G06F 16/2465* (2019.01); *G06F 16/9024* (2019.01); *G06N 5/013* (2023.01); *G16C 20/40* (2019.02)

(58) Field of Classification Search
CPC ..... G16C 20/50; G16C 20/40; G06F 16/9024; G06F 16/2465; G06N 5/006; G16F 16/9024; G16N 5/025

USPC .................................................... 702/19
See application file for complete search history.

(56) References Cited

U.S. PATENT DOCUMENTS

2010/0010946 A1\* 1/2010 De Winter et al. .... G06C 20/50
706/13

\* cited by examiner

*Primary Examiner* — Thinh T Nguyen
(74) *Attorney, Agent, or Firm* — Ariel S. Bentolila; Bay Area IP Group, LLC

(57) ABSTRACT

A method is provided to create lead compound(s) by discovering a general chemical structure, moieties, formula(s) to explore suitable compositions by computer simulation and/or robotic biological or biochemical experiments at least partially based upon employing said lead compound(s) discover method, which includes steps for inputting at least one chemical formula and at least one byproduct formula, steps for creating a list of dipeptides that might dissociate the byproduct from the input formula by way of catalysis, steps for using these dipeptides to fingerprint a protein from its peptide sequence, and searching a protein database or use experimental methods to search for such proteins. A composition creating means is provide by way of computer simulation and/or robotic biological or biochemical experiments at least partially based upon employing, as lead compound(s), the final chemical structure, moieties, formula(s) generated and communicated the above method.

6 Claims, 22 Drawing Sheets

Search Results for Enzymes to Target Benzene 1400

| Spermine | $C_{10}H_{26}N_4$ | |
|---|---|---|
| Indanidine | $C_{11}H_{13}N_5$ | |
| Quipazine | $C_{13}H_{15}N_3$ | |
| Atipamezole | $C_{14}H_{16}N_2$ | |
| Napamezole | $C_{14}H_{16}N_2$ | |
| β-bisabolene | $C_{15}H_{24}$ | |
| β-cadinene | $C_{15}H_{24}$ | |
| Δ-capnellene | $C_{15}H_{24}$ | |

| |
|---|
| MSALGVTVAL LVWAAFLLLV SMWRQVHSSW NLPPGPFPLP IIGNLFQLEL |
| KNIPKSFTRL AQRFGPVFTL YVGSQRMVVM HGYKAVKEAL LDYKDEFSGR |
| GDLPAFHAHR DRGIIFNNGP TWKDIRRFSL TTLRNYGMGK QGNESRIQRE |
| AHFLLEALRK TQGQPFDPTF LIGCAPCNVI ADILFRKHFD YNDEKFLRLM |
| YLFNENFHLL STPWLQLYNN FPSFLHYLPG SHRKVIKNVA EVKEYVSERV |
| KEHHQSLDPN CPRDLTDCLL VEMEKEKHSA ERLYTMDGIT VTVADLFFAG |
| TETTSTTLRY GLLILMKYPE IEEKLHEEID RVIGPSRIPA IKDRQEMPYM |
| DAVVHEIQRF ITLVPSNLPH EATRDTIFRG YLIPKGTVVV PTLDSVLYDN |
| QEFPDPEKFK PEHFLNENGK FKYSDYFKPF STGKRVCAGE GLARMELFLL |

FIG. 16

SYSTEM AND METHOD FOR CREATING LEAD COMPOUNDS, AND COMPOSITIONS THEREOF

CROSS-REFERENCE TO RELATED APPLICATIONS

Not applicable.

RELATED CO-PENDING U.S. PATENT APPLICATIONS

Not applicable.

INCORPORATION BY REFERENCE OF SEQUENCE LISTING PROVIDED AS A TEXT FILE

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to novel computational and/or combinatorial computer-implemented algorithmic search techniques for chemical structures, moieties, formulas and/or the like for in-silico, e.g., performed via computer simulation in reference to biological or biochemical experiments, etc., lead generation. More particularly, certain embodiments of the invention relates to algorithms to search for chemical formulas that react with or catalyze a given chemical formula as a new and useful step for in-silico lead generation of drugs outside known parts of vast chemical space, e.g., referring to the property space spanned by all possible molecules and chemical compounds adhering to a given set of construction principles and boundary conditions.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Chemical space is a concept in cheminformatics referring to the property space spanned by all possible molecules and chemical compounds adhering to a given set of construction principles and boundary conditions. It contains millions of compounds which are readily accessible and available to researchers. It is a library used in the method of molecular docking. [Source: Rudling, Axel; Gustafsson, Robert; Almlöf, Ingrid; Homan, Evert; Scobie, Martin; Warpman Berglund, Ulrika; Helleday, Thomas; Stenmark, Pål; Carlsson, Jens (Oct. 12, 2017). "Fragment-Based Discovery and Optimization of Enzyme Inhibitors by Docking of Commercial Chemical Space". Journal of Medicinal Chemistry. 60 (19): 8160-8169. doi:10.1021/acs.jmedchem.7b01006]. A chemical space often referred to in cheminformatics is that of potential pharmacologically active molecules. Its size is estimated to be in the order of $10^{60}$ molecules. Currently, there are no widely-accepted rigorous methods by the scientific community for determining the precise size of this space. The assumptions [source: Bohacek, R. S.; C. McMartin; W. C. Guida (1999). "The art and practice of structure-based drug design: A molecular modeling perspective". Medicinal Research Reviews (1): 3-50] used for estimating the number of potential pharmacologically active molecules, however, use the Lipinski rules, in particular the molecular weight limit of 500. The estimate also restricts the chemical elements used to be Carbon, Hydrogen, Oxygen, Nitrogen and Sulfur. It further makes the assumption of a maximum of 30 atoms to stay below 500 Daltons, allows for branching and a maximum of 4 rings and arrives at an estimate of $10^{63}$. This number is often misquoted in subsequent publications to be the estimated size of the whole organic chemistry space, [source: Kirkpatrick, P.; C. Ellis (2004). "Chemical space". Nature. 432 (432): 823-865.] which would be much larger if including the halogens and other elements.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that chemical libraries used for laboratory-based screening for compounds with desired properties are examples for real-world chemical libraries of small size (a few hundred to hundreds of thousands of molecules).

Systematic exploration of chemical space is possible by creating in-silico databases of virtual molecules, [source: L. Ruddigkeit; R. van Deursen; L. C. Blum; J.-L. Reymond (2012). "Enumeration of 166 Billion Organic Small Molecules in the Chemical Universe Database GDB-17". J. Chem. Inf. Model. 52 (11): 2864-2875] which can be visualized by projecting multidimensional property space of molecules in lower dimensions. [Source: M. Awale; R. van Deursen; J. L. Reymond (2013). "MQN-Mapplet: Visualization of Chemical Space with Interactive Maps of DrugBank, ChEMBL, PubChem, GDB-11, and GDB-13". J. Chem. Inf. Model. 53 (2): 509-18; L. Ruddigkeit; L. C. Blum; J.-L. Reymond (2013). "Visualization and Virtual Screening of the Chemical Universe Database GDB-17". J. Chem. Inf. Model. 53 (1): 56-65.] Generation of chemical spaces may involve creating stoichiometric combinations of electrons and atomic nuclei to yield all possible topology isomers for the given construction principles. In cheminformatics, software programs called "structure generators" may be used to generate the set of all chemical structure adhering to given boundary conditions. Constitutional isomer generators, for example, can generate all possible constitutional isomers of a given molecular gross formula.

In the real world, chemical reactions allow us to move in chemical space. The mapping between chemical space and molecular properties may often not be unique, meaning that there can be very different molecules exhibiting very similar properties. Materials design and drug discovery both involve the exploration of chemical space.

In view of the foregoing, it is clear that these traditional techniques may not be sufficient to effectively utilize currently available computational resources to best and most efficiently navigate the vastness of chemical space and thus leave room for more optimal approaches to successfully retrieve chemical formula information.

BRIEF DESCRIPTION OF THE DRAWINGS

The present invention is illustrated by way of example, and not by way of limitation, in the figures of the accompanying drawings and in which like reference numerals refer to similar elements and in which:

FIG. 14 illustrates a table of search results to target benzene, in accordance with an embodiment of the present invention;

FIG. 16 illustrates a table of enzyme displayed in codified format, in accordance with an embodiment of the present invention;

Figure 1A:
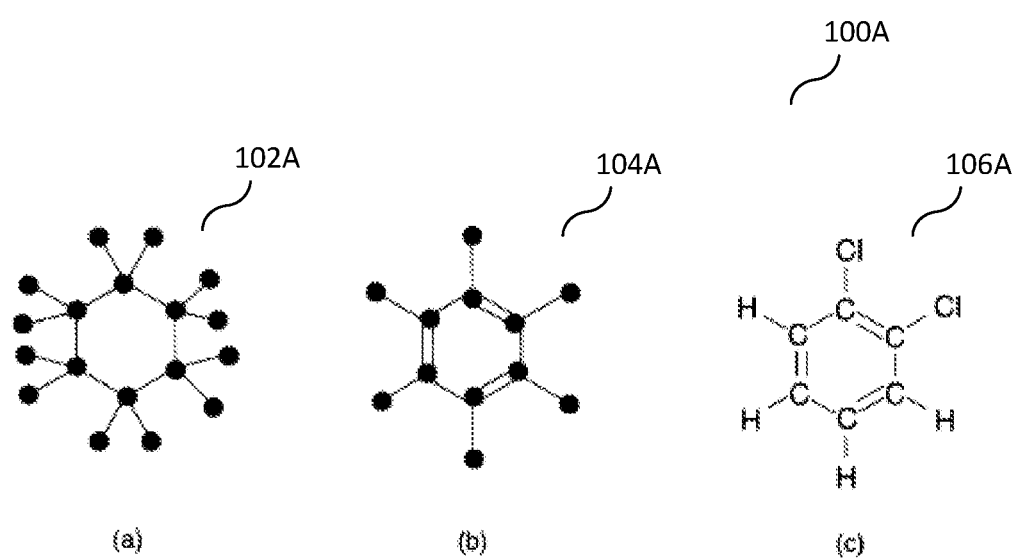
FIG. 1A illustrates a simple graph, a multigraph, and a molecular graph, respectively, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settled law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010). Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearward most point of the upper or outsole.

Similarly, the term 'substantially' is well recognized in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" include the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of. or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation.

Each term utilized herein is to be given its broadest interpretation given the context in which that term is utilized.

Terminology

The following paragraphs provide definitions and/or context for terms found in this disclosure (including the appended claims):

"Comprising" And "contain" and variations of them—Such terms are open-ended and mean "including but not limited to". When employed in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. .sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

All terms of exemplary language (e.g., including, without limitation, "such as", "like", "for example", "for instance", "similar to", etc.) are not exclusive of any other, potentially, unrelated, types of examples; thus, implicitly mean "by way of example, and not limitation . . . ", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Moreover, any claim limitation phrased in functional limitation terms covered by 35 USC § 112(6) (post AIA 112(f)) which has a preamble invoking the closed terms "consisting of," or "consisting essentially of," should be understood to mean that the corresponding structure(s) disclosed herein define the exact metes and bounds of what the so claimed invention embodiment(s) consists of, or consisting essentially of, to the exclusion of any other elements which do not materially affect the intended purpose of the so claimed embodiment(s).

Definitions

Reference to the term "chemistry" generally implies the scientific discipline involved with elements and compounds composed of atoms, molecules and ions: their composition, structure, properties, behavior and the changes they undergo during a reaction with other substances. In the scope of its subject, chemistry occupies an intermediate position between physics and biology. It is sometimes called the central science because it provides a foundation for understanding both basic and applied scientific disciplines at a fundamental level. For example, chemistry explains aspects of plant chemistry (botany), the formation of igneous rocks (geology), how atmospheric ozone is formed and how environmental pollutants are degraded (ecology), the properties of the soil on the moon (astrophysics), how medications work (pharmacology), and how to collect DNA evidence at a crime scene (forensics). Chemistry addresses topics such as how atoms and molecules interact via chemical bonds to form new chemical compounds. There are four types of chemical bonds: covalent bonds, in which compounds share one or more electron(s); ionic bonds, in which a compound donates one or more electrons to another compound to produce ions (cations and anions); hydrogen bonds; and Van der Waals force bonds. The current model of atomic structure is the quantum mechanical model. Traditional chemistry starts with the study of elementary particles, atoms, molecules, substances, metals, crystals and other aggregates of matter. This matter can be studied in solid, liquid, or gas states, in isolation or in combination. The interactions, reactions and transformations that are studied in chemistry are usually the result of interactions between atoms, leading to rearrangements of the chemical bonds which hold atoms together. Such behaviors are studied in a chemistry laboratory. The chemistry laboratory stereotypically uses various forms of laboratory glassware. However, glassware is not central to chemistry, and a great deal of experimental (as well as applied/industrial) chemistry is done without it. A chemical reaction is a transformation of some substances into one or more different substances. The basis of such a chemical transformation is the rearrangement of electrons in the chemical bonds between atoms. It can be symbolically depicted through a chemical equation, which usually involves atoms as subjects. The number of atoms on the left and the right in the equation for a chemical transformation is equal. (When the number of atoms on either side is unequal, the transformation is referred to as a nuclear reaction or radioactive decay.) The type of chemical reactions a substance may undergo and the energy changes that may accompany it are constrained by certain basic rules, known as chemical laws. Energy and entropy considerations are invariably important in almost all chemical studies. Chemical substances are classified in terms of their structure, phase, as well as their chemical compositions. They can be analyzed using the tools of chemical analysis, e.g. spectroscopy and chromatography. Scientists engaged in chemical research are known as chemists. Most chemists specialize in one or more sub-disciplines.

Reference to the term "chemical reaction" generally implies a process that leads to the chemical transformation of one set of chemical substances to another.[1] Classically, chemical reactions encompass changes that only involve the positions of electrons in the forming and breaking of chemical bonds between atoms, with no change to the nuclei (no change to the elements present), and can often be described by a chemical equation. Nuclear chemistry is a sub-discipline of chemistry that involves the chemical reactions of unstable and radioactive elements where both electronic and nuclear changes can occur. The substance (or substances) initially involved in a chemical reaction are called reactants or reagents. Chemical reactions are usually characterized by a chemical change, and they yield one or more products, which usually have properties different from the reactants. Reactions often consist of a sequence of individual sub-steps, the so-called elementary reactions, and the information on the precise course of action is part of the reaction mechanism. Chemical reactions are described with chemical equations, which symbolically present the starting materials, end products, and sometimes intermediate products and reaction conditions. Chemical reactions happen at a characteristic reaction rate at a given temperature and chemical concentration. Typically, reaction rates increase with increasing temperature because there is more thermal energy available to reach the activation energy necessary for breaking bonds between atoms. Reactions may proceed in the forward or reverse direction until they go to completion or reach equilibrium. Reactions that proceed in the forward direction to approach equilibrium are often described as spontaneous, requiring no input of free energy to go forward. Non-spontaneous reactions require input of free energy to go forward (examples include charging a battery by applying an external electrical power source, or photosynthesis driven by absorption of electromagnetic radiation in the form of sunlight). Different chemical reactions are used in combinations during chemical synthesis in order to obtain a desired product. In biochemistry, a consecutive series of chemical reactions (where the product of one reaction is the reactant of the next reaction) form metabolic pathways. These reactions are often catalyzed by protein enzymes. Enzymes increase the rates of biochemical reactions, so that metabolic syntheses and decompositions impossible under ordinary conditions can occur at the temperatures and concentrations present within a cell. The general concept of a chemical reaction has been extended to reactions between entities smaller than atoms, including nuclear reactions, radioactive decays, and reactions between elementary particles, as described by quantum field theory.

Reference to the term "chemical equation" generally implies the symbolic representation of a chemical reaction in the form of symbols and formulae, wherein the reactant entities are given on the left-hand side and the product entities on the right-hand side. The coefficients next to the symbols and formulae of entities are the absolute values of the stoichiometric numbers. A chemical equation consists of the chemical formulas of the reactants (the starting substances) and the chemical formula of the products (substances formed in the chemical reaction). The two are separated by an arrow symbol (→, usually read as "yields") and each individual substance's chemical formula is separated from others by a plus sign. As an example, the equation for the reaction of hydrochloric acid with sodium can be denoted: 2 HCl+2 Na→2 NaCl+$H_2$. This equation would be read as "two HCl plus two Na yields two NaCl and H two." But, for equations involving complex chemicals, rather than reading the letter and its subscript, the chemical formulas are read using IUPAC nomenclature. Using IUPAC nomenclature, this equation would be read as "hydrochloric acid plus sodium yields sodium chloride and hydrogen gas." This equation indicates that sodium and HCl react to form NaCl and $H_2$. It also indicates that two sodium molecules are required for every two hydrochloric acid molecules and the reaction will form two sodium chloride molecules and one diatomic molecule of hydrogen gas molecule for every two hydrochloric acid and two sodium molecules that react. The stoichiometric coefficients (the numbers in front of the chemical formulas) result from the law of conservation of mass and the law of conservation of charge (see "Balancing Chemical Equation" section below for more information).

Reference to the term "chemical engineering" generally implies a branch of engineering that uses principles of chemistry, physics, mathematics, biology, and economics to efficiently use, produce, design, transport and transform energy and materials. The work of chemical engineers can range from the utilization of nano-technology and nanomaterials in the laboratory to large-scale industrial processes that convert chemicals, raw materials, living cells, microorganisms, and energy into useful forms and products. Chemical engineers are involved in many aspects of plant design and operation, including safety and hazard assessments, process design and analysis, modeling, control engineering, chemical reaction engineering, nuclear engineering, biological engineering, construction specification, and operating instructions. Chemical engineers typically hold a degree in Chemical Engineering or Process Engineering. Practicing engineers may have professional certification and be accredited members of a professional body. Such bodies include the Institution of Chemical Engineers (IChemE) or the American Institute of Chemical Engineers (AIChE). A degree in chemical engineering is directly linked with all of the other engineering disciplines, to various extents. Reference to the term "biochemistry" generally implies the study of chemical processes within and relating to living organisms. Biochemical processes give rise to the complexity of life. A sub-discipline of both biology and chemistry, biochemistry can be divided in three fields; molecular genetics, protein science and metabolism. Over the last decades of the 20th century, biochemistry has through these three disciplines become successful at explaining living processes. Almost all areas of the life sciences are being uncovered and developed by biochemical methodology and research. Biochemistry focuses on understanding how biological molecules give rise to the processes that occur within living cells and between cells, which in turn relates greatly to the study and understanding of tissues, organs, and organism structure and function. Biochemistry is closely related to molecular biology, the study of the molecular mechanisms of biological phenomena. Much of biochemistry deals with the structures, functions and interactions of biological macromolecules, such as proteins, nucleic acids, carbohydrates and lipids, which provide the structure of cells and perform many of the functions associated with life. The chemistry of the cell also depends on the reactions of smaller molecules and ions. These can be inorganic, for example water and metal ions, or organic, for example the amino acids, which are used to synthesize proteins. The mechanisms by which cells harness energy from their environment via chemical reactions are known as metabolism. The findings of biochemistry are applied primarily in medicine, nutrition, and agriculture. In medicine, biochemists investigate the causes and cures of diseases. In nutrition, they study how to maintain health wellness and study the effects of nutritional deficiencies. In agriculture, biochemists investigate soil and fertilizers, and try to discover ways to improve crop cultivation, crop storage and pest control.

Reference to the term "molecular genetics" implies the field of biology that studies the structure and function of genes at a molecular level and thus employs methods of both molecular biology and genetics. The study of chromosomes and gene expression of an organism can give insight into heredity, genetic variation, and mutations. This is useful in the study of developmental biology and in understanding and treating genetic diseases.

Reference to the term "proteins" generally implies large biomolecules, or macromolecules, consisting of one or more long chains of amino acid residues. Proteins perform a vast array of functions within organisms, including catalyzing metabolic reactions, DNA replication, responding to stimuli, providing structure to cells and organisms, and transporting molecules from one location to another. Proteins differ from one another primarily in their sequence of amino acids, which is dictated by the nucleotide sequence of their genes, and which usually results in protein folding into a specific three-dimensional structure that determines its activity. A linear chain of amino acid residues is called a polypeptide. A protein contains at least one long polypeptide. Short polypeptides, containing less than 20-30 residues, are rarely considered to be proteins and are commonly called peptides, or sometimes oligopeptides. The individual amino acid residues are bonded together by peptide bonds and adjacent amino acid residues. The sequence of amino acid residues in a protein is defined by the sequence of a gene, which is encoded in the genetic code. In general, the genetic code specifies 20 standard amino acids; however, in certain organisms the genetic code can include selenocysteine and—in certain archaea—pyrrolysine. Shortly after or even during synthesis, the residues in a protein are often chemically modified by post-translational modification, which alters the physical and chemical properties, folding, stability, activity, and ultimately, the function of the proteins. Sometimes proteins have non-peptide groups attached, which can be called prosthetic groups or cofactors. Proteins can also work together to achieve a particular function, and they often associate to form stable protein complexes. Once formed, proteins only exist for a certain period and are then degraded and recycled by the cell's machinery through the process of protein turnover. A protein's lifespan is measured in terms of its half-life and covers a wide range. They can exist for minutes or years with an average lifespan of 1-2 days in mammalian cells. Abnormal or misfolded proteins are degraded more rapidly either due to being targeted for destruction or due to being unstable. Like other biological macromolecules such as polysaccharides and nucleic acids, proteins are essential parts of organisms and participate in virtually every process within cells. Many proteins are enzymes that catalyze biochemical reactions and are vital to metabolism. Proteins also have structural or mechanical functions, such as actin and myosin in muscle and the proteins in the cytoskeleton, which form a system of scaffolding that maintains cell shape. Other proteins are important in cell signaling, immune responses, cell adhesion, and the cell cycle. In animals, proteins are needed in the diet to provide the essential amino acids that cannot be synthesized. Digestion breaks the proteins down for use in the metabolism. Proteins may be purified from other cellular components using a variety of techniques such as ultracentrifugation, precipitation, electrophoresis, and chromatography; the advent of genetic engineering has made possible a number of methods to facilitate purification. Methods commonly used to study protein structure and function include immunohistochemistry, site-directed mutagenesis, X-ray crystallography, nuclear magnetic resonance and mass spectrometry.

Reference to the term "metabolism" generally implies the set of life-sustaining chemical reactions in organisms. The three main purposes of metabolism are: the conversion of food to energy to run cellular processes; the conversion of food/fuel to building blocks for proteins, lipids, nucleic acids, and some carbohydrates; and the elimination of nitrogenous wastes. These enzyme-catalyzed reactions allow organisms to grow and reproduce, maintain their structures, and respond to their environments. (The word metabolism can also refer to the sum of all chemical reactions that occur in living organisms, including digestion and the transport of substances into and between different cells, in which case the above described set of reactions within the cells is called intermediary metabolism or intermediate metabolism). Metabolic reactions may be categorized as catabolic—the breaking down of compounds (for example, the breaking down of glucose to pyruvate by cellular respiration); or anabolic—the building up (synthesis) of compounds (such as proteins, carbohydrates, lipids, and nucleic acids). Usually, catabolism releases energy, and anabolism consumes energy. The chemical reactions of metabolism are organized into metabolic pathways, in which one chemical is transformed through a series of steps into another chemical, each step being facilitated by a specific enzyme. Enzymes are crucial to metabolism because they allow organisms to drive desirable reactions that require energy that will not occur by themselves, by coupling them to spontaneous reactions that release energy. Enzymes act as catalysts—they allow a reaction to proceed more rapidly—and they also allow the regulation of the rate of a metabolic reaction, for example in response to changes in the cell's environment or to signals from other cells. The metabolic system of a particular organism determines which substances it will find nutritious and which poisonous. For example, some prokaryotes use hydrogen sulfide as a nutrient, yet this gas is poisonous to animals. The basal metabolic rate of an organism is the measure of the amount of energy consumed by all of these chemical reactions. A striking feature of metabolism is the similarity of the basic metabolic pathways among vastly different species. For example, the set of carboxylic acids that are best known as the intermediates in the citric acid cycle are present in all known organisms, being found in species as diverse as the unicellular bacterium *Escherichia coli* and huge multicellular organisms like elephants. These similarities in metabolic pathways are likely due to their early appearance in evolutionary history, and their retention because of their efficacy.

Reference to the term "biochemical engineering" generally implies a field of study with roots stemming from chemical engineering and biological engineering. It mainly deals with the design, construction, and advancement of unit processes that involve biological organisms or organic molecules and has various applications in areas of interest such as biofuels, food, pharmaceuticals, biotechnology, and water treatment processes. The role of a biochemical engineer is to take findings developed by biologists and chemists in a laboratory and translate that to a large-scale manufacturing process. Reference to the term "bioinformatics" generally implies an interdisciplinary field that develops methods and software tools for understanding biological data. As an interdisciplinary field of science, bioinformatics combines biology, computer science, information engineering, mathematics and statistics to analyze and interpret biological data. Bioinformatics has been used for in silico analyses of biological queries using mathematical and statistical techniques. Bioinformatics is both an umbrella term for the body of biological studies that use computer programming as part of their methodology, as well as a reference to specific analysis "pipelines" that are repeatedly used, particularly in the field of genomics. Common uses of bioinformatics include the identification of candidates' genes and single nucleotide polymorphisms (SNPs). Often, such identification is made with the aim of better understanding the genetic basis of disease, unique adaptations, desirable properties (esp. in agricultural species), or differences between populations. In a less formal way, bioinformatics also tries to understand the organizational principles within nucleic acid and protein sequences, called proteomics. To study how normal cellular activities are altered in different disease states, the biological data must be combined to form a comprehensive picture of these activities. Therefore, the field of bioinformatics has evolved such that the most pressing task now involves the analysis and interpretation of various types of data. This includes nucleotide and amino acid sequences, protein domains, and protein structures. The actual process of analyzing and interpreting data is referred to as computational biology. Important sub-disciplines within bioinformatics and computational biology include: development and implementation of computer programs that enable efficient access to, use and management of, various types of information; and, development of new algorithms (mathematical formulas) and statistical measures that assess relationships among members of large data sets. For example, there are methods to locate a gene within a sequence, to predict protein structure and/or function, and to cluster protein sequences into families of related sequences. The primary goal of bioinformatics is to increase the understanding of biological processes. What sets it apart from other approaches, however, is its focus on developing and applying computationally intensive techniques to achieve this goal. Examples include: pattern recognition, data mining, machine learning algorithms, and visualization. Major research efforts in the field include sequence alignment, gene finding, genome assembly, drug design, drug discovery, protein structure alignment, protein structure prediction, prediction of gene expression and protein-protein interactions, genome-wide association studies, the modeling of evolution and cell division/mitosis. Bioinformatics now entails the creation and advancement of databases, algorithms, computational and statistical techniques, and theory to solve formal and practical problems arising from the management and analysis of biological data. Over the past few decades, rapid developments in genomic and other molecular research technologies and developments in information technologies have combined to produce a tremendous amount of information related to molecular biology. Bioinformatics is the name given to these mathematical and computing approaches used to glean understanding of biological processes. Common activities in bioinformatics include mapping and analyzing DNA and protein sequences, aligning DNA and protein sequences to compare them, and creating and viewing 3-D models of protein structures.

Reference to the term "cheminformatics" generally implies the use of computer and informational techniques applied to a range of problems in the field of chemistry. These in silico techniques are used, for example, in pharmaceutical companies and academic settings in the process of drug discovery. These methods can also be used in chemical and allied industries in various other forms. The primary application of cheminformatics is in the storage, indexing and search of information relating to compounds. The efficient search of such stored information includes topics that are dealt with in computer science as data mining, information retrieval, information extraction and machine learning. Related research topics include: unstructured data; information retrieval; information extraction; structured data mining and mining of structured data; database mining; graph mining; molecule mining; sequence mining; tree mining; and, digital libraries. Chemical data can pertain to real or virtual molecules. Virtual libraries of compounds may be generated in various ways to explore chemical space and hypothesize novel compounds with desired properties. Virtual libraries of classes of compounds (drugs, natural products, diversity-oriented synthetic products) were recently generated using the FOG (fragment optimized growth) algorithm. This was done by using cheminformatic tools to train transition probabilities of a Markov chain on authentic classes of compounds, and then using the Markov chain to generate novel compounds that were similar to the training database.

Reference to the term "in silico" (e.g., pseudo-latin for "in silicon", alluding to the mass use of silicon for computer chips) generally implies an expression meaning "performed on computer or via computer simulation" in reference to biological experiments. The phrase was coined in 1989 as an allusion to the Latin phrases in vivo, in vitro, and in situ, which are commonly used in biology (see also systems biology) and refer to experiments done in living organisms, outside living organisms, and where they are found in nature, respectively.

Reference to the term "drug discovery" generally implies he process by which new candidate medications are discovered. Historically, drugs were discovered by identifying the active ingredient from traditional remedies or by serendipitous discovery, as with penicillin. More recently, chemical libraries of synthetic small molecules, natural products or extracts were screened in intact cells or whole organisms to identify substances that had a desirable therapeutic effect in a process known as classical pharmacology. After sequencing of the human genome allowed rapid cloning and synthesis of large quantities of purified proteins, it has become common practice to use high throughput screening of large compounds libraries against isolated biological targets which are hypothesized to be disease-modifying in a process known as reverse pharmacology. Hits from these screens are then tested in cells and then in animals for efficacy. Modern drug discovery involves the identification of screening hits, medicinal chemistry and optimization of those hits to increase the affinity, selectivity (to reduce the potential of side effects), efficacy/potency, metabolic stability (to increase the half-life), and oral bioavailability. Once a compound that fulfills all of these requirements has been identified, the process of drug development can continue, and, if successful, clinical trials. One or more of these steps may, but not necessarily, involve computer-aided drug design. Modern drug discovery is thus usually a capital-intensive process that involves large investments by pharmaceutical industry corporations as well as national governments (who provide grants and loan guarantees).

Reference to the term "computational science" generally implies a rapidly growing multidisciplinary field that uses advanced computing capabilities to understand and solve complex problems. It is an area of science which spans many disciplines, but at its core it involves the development of models and simulations to understand natural systems and may include: algorithms (numerical and non-numerical), mathematical models, computational models, and computer simulations developed to solve science (e.g., biological, physical, and social), engineering, and humanities problems; computer and information science that develops and optimizes the advanced system hardware, software, networking, data management components needed to solve computationally demanding problems; and, computing infrastructure that supports both the science and engineering problem solving and the developmental computer and information science. In practical use, it is typically the application of computer simulation and other forms of computation from numerical analysis and theoretical computer science to solve problems in various scientific disciplines. The field is different from theory and laboratory experiment which are the traditional forms of science and engineering. The scientific computing approach is to gain understanding, mainly through the analysis of mathematical models implemented on computers. Scientists and engineers develop computer programs, application software, that model systems being studied and run these programs with various sets of input parameters. The essence of computational science is the application of numerical algorithms and/or computational mathematics. In some cases, these models require massive amounts of calculations (usually floating-point) and are often executed on supercomputers or distributed computing platforms.

Reference to the term "chemical graph theory" generally implies the topology branch of mathematical chemistry which applies graph theory to mathematical modeling of chemical phenomena.

Reference to the term "data mining" generally implies the process of discovering patterns in large data sets involving methods at the intersection of machine learning, statistics, and database systems. Data mining is an interdisciplinary subfield of computer science and statistics with an overall goal to extract information (with intelligent methods) from a data set and transform the information into a comprehensible structure for further use. Data mining is the analysis step of the "knowledge discovery in databases" process, or KDD. Aside from the raw analysis step, it also involves database and data management aspects, data pre-processing, model and inference considerations, interestingness metrics, complexity considerations, post-processing of discovered structures, visualization, and online updating. The difference between data analysis and data mining is that data analysis is used to test models and hypotheses on the dataset, e.g., analyzing the effectiveness of a marketing campaign, regardless of the amount of data; in contrast, data mining uses machine-learning and statistical models to uncover clandestine or hidden patterns in a large volume of data. The term "data mining" is in fact a misnomer, because the goal is the extraction of patterns and knowledge from large amounts of data, not the extraction (mining) of data itself. It also is a buzzword and is frequently applied to any form of large-scale data or information processing (collection, extraction, warehousing, analysis, and statistics) as well as any application of computer decision support system, including artificial intelligence (e.g., machine learning) and business intelligence. The actual data mining task is the semi-automatic or automatic analysis of large quantities of data to extract previously unknown, interesting patterns such as groups of data records (cluster analysis), unusual records (anomaly detection), and dependencies (association rule mining, sequential pattern mining). This usually involves using database techniques such as spatial indices. These patterns can then be seen as a kind of summary of the input data, and may be used in further analysis or, for example, in machine learning and predictive analytics. For example, the data mining step might identify multiple groups in the data, which can then be used to obtain more accurate prediction results by a decision support system. Neither the data collection, data preparation, nor result interpretation and reporting is part of the data mining step, but do belong to the overall KDD process as additional steps. The related terms data dredging, data fishing, and data snooping refer to the use of data mining methods to sample parts of a larger population data set that are (or may be) too small for reliable statistical inferences to be made about the validity of any patterns discovered. These methods can, however, be used in creating new hypotheses to test against the larger data populations.

Reference to the term "chemical space" generally implies a concept in cheminformatics referring to the property space spanned by all possible molecules and chemical compounds adhering to a given set of construction principles and boundary conditions. It contains millions of compounds which are readily accessible and available to researchers. It is a library used in the method of molecular docking.

Reference to the term "docking" in molecular modeling generally implies a method which predicts the preferred orientation of one molecule to a second when bound to each other to form a stable complex.[1] Knowledge of the preferred orientation in turn may be used to predict the strength of association or binding affinity between two molecules using, for example, scoring functions. The associations between biologically relevant molecules such as proteins, peptides, nucleic acids, carbohydrates, and lipids play a central role in signal transduction. Furthermore, the relative orientation of the two interacting partners may affect the type of signal produced (e.g., agonism vs antagonism). Therefore, docking is useful for predicting both the strength and type of signal produced. Molecular docking is one of the most frequently used methods in structure-based drug design, due to its ability to predict the binding-conformation of small molecule ligands to the appropriate target binding site. Characterization of the binding behavior plays an important role in rational design of drugs as well as to elucidate fundamental biochemical processes. Reference to the term "information retrieval" generally implies the activity of obtaining information system resources that are relevant to an information need from a collection of those resources. Searches can be based on full-text or other content-based indexing. Information retrieval is the science of searching for information in a document, searching for documents themselves, and also searching for the metadata that describes data, and for databases of texts, images or sounds. Automated information retrieval systems are used to reduce what has been called information overload. An IR system is a software system that provides access to books, journals and other documents; stores and manages those documents. Web search engines are the most visible IR applications. An information retrieval process begins when a user enters a query into the system. Queries are formal statements of information needs, for example search strings in web search engines. In information retrieval a query does not uniquely identify a single object in the collection. Instead, several objects may match the query, perhaps with different degrees of relevancy. An object is an entity that is represented by information in a content collection or database. User queries are matched against the database information. However, as opposed to classical SQL queries of a database, in information retrieval the results returned may or may not match the query, so results are typically ranked. This ranking of results is a key difference of information retrieval searching compared to database searching. Depending on the application the data objects may be, for example, text documents, images, audio, mind maps or videos. Often the documents themselves are not kept or stored directly in the IR system, but are instead represented in the system by document surrogates or metadata. Most IR systems compute a numeric score on how well each object in the database matches the query, and rank the objects according to this value. The top ranking objects are then shown to the user. The process may then be iterated if the user wishes to refine the query.

Reference to the term "structure mining" generally implies the process of finding and extracting useful information from semi-structured data sets. Graph mining, sequential pattern mining and molecule mining are special cases of structured data mining.

Reference to the term "molecule mining" generally implies that since molecules may be represented by molecular graphs, this capability is strongly related to graph mining and structured data mining. The main problem is how to represent molecules while discriminating the data instances.

One way to do this is chemical similarity metrics, which has a long tradition in the field of cheminformatics.

Typical approaches to calculate chemical similarities use chemical fingerprints, but this loses the underlying information about the molecule topology. Mining the molecular graphs directly avoids this problem. So does the inverse QSAR problem which is preferable for vectoral mappings.

Reference to the term "sequential pattern mining" generally implies a topic of data mining concerned with finding statistically relevant patterns between data examples where the values are delivered in a sequence. It is usually presumed that the values are discrete, and thus time series mining is closely related, but usually considered a different activity. Sequential pattern mining is a special case of structured data mining.

There are several key traditional computational problems addressed within this field. These include building efficient databases and indexes for sequence information, extracting the frequently occurring patterns, comparing sequences for similarity, and recovering missing sequence members. In general, sequence mining problems can be classified as string mining which is typically based on string processing algorithms and itemset mining which is typically based on association rule learning. Local process models extend sequential pattern mining to more complex patterns that can include (exclusive) choices, loops, and concurrency constructs in addition to the sequential ordering construct.

Reference to the term "chemical genomics" generally implies the systematic screening of targeted chemical libraries of small molecules against individual drug target families (e.g., GPCRs, nuclear receptors, kinases, proteases, etc.) with the ultimate goal of identification of novel drugs and drug targets. Typically, some members of a target library have been well characterized where both the function has been determined and compounds that modulate the function of those targets (ligands in the case of receptors, inhibitors of enzymes, or blockers of ion channels) have been identified. Other members of the target family may have unknown function with no known ligands and hence are classified as orphan receptors. By identifying screening hits that modulate the activity of the less well characterized members of the target family, the function of these novel targets can be elucidated. Furthermore, the hits for these targets can be used as a starting point for drug discovery. The completion of the human genome project has provided an abundance of potential targets for therapeutic intervention. Chemogenomics strives to study the intersection of all possible drugs on all of these potential targets. A common method to construct a targeted chemical library is to include known ligands of at least one and preferably several members of the target family. Since a portion of ligands that were designed and synthesized to bind to one family member will also bind to additional family members, the compounds contained in a targeted chemical library should collectively bind to a high percentage of the target family.

Reference to the term "computational chemistry" generally implies a branch of chemistry that uses computer simulation to assist in solving chemical problems. It uses methods of theoretical chemistry, incorporated into efficient computer programs, to calculate the structures and properties of molecules and solids. It is necessary because, apart from relatively recent results concerning the hydrogen molecular ion (dihydrogen cation, see references therein for more details), the quantum many-body problem cannot be solved analytically, much less in closed form. While computational results normally complement the information obtained by chemical experiments, it can in some cases predict hitherto unobserved chemical phenomena. It is widely used in the design of new drugs and materials. Examples of such properties are structure (i.e., the expected positions of the constituent atoms), absolute and relative (interaction) energies, electronic charge density distributions, dipoles and higher multipole moments, vibrational frequencies, reactivity, or other spectroscopic quantities, and cross sections for collision with other particles. The methods used cover both static and dynamic situations. In all cases, the computer time and other resources (such as memory and disk space) increase rapidly with the size of the system being studied. That system can be one molecule, a group of molecules, or a solid. Computational chemistry methods range from very approximate to highly accurate; the latter are usually feasible for small systems only. Ab initio methods are based entirely on quantum mechanics and basic physical constants. Other methods are called empirical or semi-empirical because they use additional empirical parameters. Both ab initio and semi-empirical approaches involve approximations. These range from simplified forms of the first-principles equations that are easier or faster to solve, to approximations limiting the size of the system (for example, periodic boundary conditions), to fundamental approximations to the underlying equations that are required to achieve any solution to them at all. For example, most ab initio calculations make the Born-Oppenheimer approximation, which greatly simplifies the underlying Schrödinger equation by assuming that the nuclei remain in place during the calculation. In principle, ab initio methods eventually converge to the exact solution of the underlying equations as the number of approximations is reduced. In practice, however, it is impossible to eliminate all approximations, and residual error inevitably remains. The goal of computational chemistry is to minimize this residual error while keeping the calculations tractable. In some cases, the details of electronic structure are less important than the long-time phase space behavior of molecules. This is the case in conformational studies of proteins and protein-ligand binding thermodynamics. Classical approximations to the potential energy surface are used, as they are computationally less intensive than electronic calculations, to enable longer simulations of molecular dynamics. Furthermore, cheminformatics uses even more empirical (and computationally cheaper) methods like machine learning based on physicochemical properties. One typical problem in cheminformatics is to predict the binding affinity of drug molecules to a given target.

Reference to the term "information engineering" generally implies the engineering discipline that deals with the generation, distribution, analysis, and use of information, data, and knowledge in systems. The field first became identifiable in the early 21st century. The components of information engineering include more theoretical fields such as machine learning, artificial intelligence, control theory, signal processing, and information theory, and more applied fields such as computer vision, natural language processing, bioinformatics, medical image computing, cheminformatics, autonomous robotics, mobile robotics, and telecommunications. Many of these originate from computer science, as well as other branches of engineering such as computer engineering, electrical engineering, and bioengineering. The field of information engineering is based heavily on mathematics, particularly probability, statistics, calculus, linear algebra, optimization, differential equations, variational calculus, and complex analysis. Information engineers often hold a degree in information engineering or a related area, and are often part of a professional body such as the Institution of Engineering and Technology or Institute of Measurement and Control. They are employed in almost all industries due to the widespread use of information engineering.

Reference to the term "molecular design software" generally implies software for molecular modeling, that provides special support for developing molecular models de novo. In contrast to the usual molecular modeling programs, such as for molecular dynamics and quantum chemistry, such software directly supports the aspects related to constructing molecular models, including: molecular graphics; interactive molecular drawing and conformational editing; building polymeric molecules, crystals, and solvated systems; partial charges development; geometry optimization; and, support for the different aspects of force field development.

Reference to the term "molecular graphics" generally implies the discipline and philosophy of studying molecules and their properties through graphical representation.

Reference to the term "molecular modeling" generally implies methods, theoretical and computational, used to model or mimic the behavior of molecules. The methods are used in the fields of computational chemistry, drug design, computational biology and materials science to study molecular systems ranging from small chemical systems to large biological molecules and material assemblies. The simplest calculations can be performed by hand, but inevitably computers are required to perform molecular modeling of any reasonably sized system. The common feature of molecular modeling methods is the atomistic level description of the molecular systems. This may include treating atoms as the smallest individual unit (a molecular mechanics approach), or explicitly modeling protons and neutrons with its quarks, anti-quarks and gluons and electrons with its photons (a quantum chemistry approach).

Reference to the term "nanoinformatics" generally implies the application of informatics to nanotechnology. It is an interdisciplinary field that develops methods and software tools for understanding nanomaterials, their properties, and their interactions with biological entities, and using that information more efficiently. It differs from cheminformatics in that nanomaterials usually involve nonuniform collections of particles that have distributions of physical properties that must be specified. The nanoinformatics infrastructure includes ontologies for nanomaterials, file formats, and data repositories. Nanoinformatics has applications for improving workflows in fundamental research, manufacturing, and environmental health, allowing the use of high-throughput data-driven methods to analyze broad sets of experimental results. Nanomedicine applications include analysis of nanoparticle-based pharmaceuticals for structure-activity relationships in a similar manner to bioinformatics.

Reference to the term "enzymes" generally implies macromolecular biological catalysts that accelerate chemical reactions. The molecules upon which enzymes may act are called substrates, and the enzyme converts the substrates into different molecules known as products. Almost all metabolic processes in the cell need enzyme catalysis in order to occur at rates fast enough to sustain life. Metabolic pathways depend upon enzymes to catalyze individual steps. The study of enzymes is called enzymology and a new field of pseudo-enzyme analysis has recently grown up, recognizing that during evolution, some enzymes have lost the ability to carry out biological catalysis, which is often reflected in their amino acid sequences and unusual 'pseudocatalytic' properties. Enzymes are known to catalyze more than 5,000 biochemical reaction types. Most enzymes are proteins, although a few are catalytic RNA molecules. The latter are called ribozymes. Enzymes' specificity comes from their unique three-dimensional structures. Like all catalysts, enzymes increase the reaction rate by lowering its activation energy. Some enzymes can make their conversion of substrate to product occur many millions of times faster. An extreme example is orotidine 5'-phosphate decarboxylase, which allows a reaction that would otherwise take millions of years to occur in milliseconds. Chemically, enzymes are like any catalyst and are not consumed in chemical reactions, nor do they alter the equilibrium of a reaction. Enzymes differ from most other catalysts by being much more specific. Enzyme activity can be affected by other molecules: inhibitors are molecules that decrease enzyme activity, and activators are molecules that increase activity. Many therapeutic drugs and poisons are enzyme inhibitors. An enzyme's activity decreases markedly outside its optimal temperature and pH, and many enzymes are (permanently) denatured when exposed to excessive heat, losing their structure and catalytic properties. Some enzymes are used commercially, for example, in the synthesis of antibiotics. Some household products use enzymes to speed up chemical reactions: enzymes in biological washing powders break down protein, starch or fat stains on clothes, and enzymes in meat tenderizer break down proteins into smaller molecules, making the meat easier to chew.

Reference to the term "isomer" generally implies ions or molecules with identical formulas but distinct structures. Isomers do not necessarily share similar properties. Two main forms of isomerism are structural isomerism (or constitutional isomerism) and stereoisomerism (or spatial isomerism).

Reference to the term "structural analog" generally implies a chemical analog or simply an analog, is a compound having a structure similar to that of another compound, but differing from it in respect to a certain component. It can differ in one or more atoms, functional groups, or substructures, which are replaced with other atoms, groups, or substructures. A structural analog can be imagined to be formed, at least theoretically, from the other compound. Structural analogs are often isoelectronic. Despite a high chemical similarity, structural analogs are not necessarily functional analogs and can have very different physical, chemical, biochemical, or pharmacological properties. In drug discovery either a large series of structural analogs of an initial lead compound are created and tested as part of a structure-activity relationship study or a database is screened for structural analogs of a lead compound. Chemical analogues of illegal drugs are developed and sold in order to circumvent laws. Such substances are often called designer drugs. Because of this, the United States passed the Federal Analogue Act in 1986. This bill banned the production of any chemical analogue of a Schedule I or Schedule II substance that has substantially similar pharmacological effects, with the intent of human consumption.

Reference to the term "stereoisomerism" generally implies a form of isomerism in which molecules have the same molecular formula and sequence of bonded atoms (constitution), but differ in the three-dimensional orientations of their atoms in space. This contrasts with structural isomers, which share the same molecular formula, but the bond connections or their order differs. By definition, molecules that are stereoisomers of each other represent the same structural isomer.

Reference to the term "euclidean distance" generally implies the "ordinary" straight-line distance between two points in Euclidean space. With this distance, Euclidean space becomes a metric space. The associated norm is called the Euclidean norm.

Reference to the term "benzene" generally implies an organic chemical compound with the chemical formula $C_6H_6$. The benzene molecule is composed of six carbon atoms joined in a ring with one hydrogen atom attached to each. As it contains only carbon and hydrogen atoms, benzene is classed as a hydrocarbon.

Reference to the term "dipeptide" generally implies an organic compound derived from two amino acids. The constituent amino acids can be the same or different. When different, two isomers of the dipeptide are possible, depending on the sequence. Several dipeptides are physiologically important, and some are both physiologically and commercially significant. A well-known dipeptide is aspartame, an artificial sweetener.

Dipeptides are white solids. Many are far more water-soluble than the parent amino acids. For example, the dipeptide Ala-Gln has the solubility of 586 g/L more than 10× the solubility of Gln (35 g/L). Dipeptides also can exhibit different stabilities, e.g. with respect to hydrolysis. Gln does not withstand, sterilization procedures, whereas this dipeptide does. Because dipeptides are prone to hydrolysis, the high solubility is exploited in infusions, i.e. to provide nutrition.

Devices or system modules that are in at least general communication with each other need not be in continuous communication with each other, unless expressly specified otherwise. In addition, devices or system modules that are in at least general communication with each other may communicate directly or indirectly through one or more intermediaries. Moreover, it is understood that any system components described or named in any embodiment or claimed herein may be grouped or sub-grouped (and accordingly implicitly renamed) in any combination or sub-combination as those skilled in the art can imagine as suitable for the particular application, and still be within the scope and spirit of the claimed embodiments of the present invention. For an example of what this means, if the invention was a controller of a motor and a valve and the embodiments and claims articulated those components as being separately grouped and connected, applying the foregoing would mean that such an invention and claims would also implicitly cover the valve being grouped inside the motor and the controller being a remote controller with no direct physical connection to the motor or internalized valve, as such the claimed invention is contemplated to cover all ways of grouping and/or adding of intermediate components or systems that still substantially achieve the intended result of the invention.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s)

of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

Those of skill in the art will appreciate that where appropriate, some embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Where appropriate, embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

"Software" may refer to prescribed rules to operate a computer. Examples of software may include: code segments in one or more computer-readable languages; graphical and or/textual instructions; applets; pre-compiled code; interpreted code; compiled code; and computer programs.

While embodiments herein may be discussed in terms of a processor having a certain number of bit instructions/data, those skilled in the art will know others that may be suitable such as 16 bits, 32 bits, 64 bits, 128 s or 256 bit processors or processing, which can usually alternatively be used. Where a specified logical sense is used, the opposite logical sense is also intended to be encompassed.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A network is a collection of links and nodes (e.g., multiple computers and/or other devices connected together) arranged so that information may be passed from one part of the network to another over multiple links and through various nodes. Examples of networks include the Internet, the public switched telephone network, the global Telex network, computer networks (e.g., an intranet, an extranet, a local-area network, or a wide-area network), wired networks, and wireless networks.

The Internet is a worldwide network of computers and computer networks arranged to allow the easy and robust exchange of information between computer users. Hundreds of millions of people around the world have access to computers connected to the Internet via Internet Service Providers (ISPs). Content providers (e.g., website owners or operators) place multimedia information (e.g., text, graphics, audio, video, animation, and other forms of data) at specific locations on the Internet referred to as webpages. Websites comprise a collection of connected, or otherwise related, webpages. The combination of all the websites and their corresponding webpages on the Internet is generally known as the World Wide Web (WWW) or simply the Web.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically, a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, removable media, flash memory, a "memory stick", any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

A "computer system" may refer to a system having one or more computers, where each computer may include a computer-readable medium embodying software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet.

As used herein, the "client-side" application should be broadly construed to refer to an application, a page associated with that application, or some other resource or function invoked by a client-side request to the application. A "browser" as used herein is not intended to refer to any specific browser (e.g., Internet Explorer, Safari, FireFox, or the like), but should be broadly construed to refer to any client-side rendering engine that can access and display Internet-accessible resources. A "rich" client typically refers to a non-HTTP based client-side application, such as an SSH or CFIS client. Further, while typically the client-server interactions occur using HTTP, this is not a limitation either. The client server interaction may be formatted to conform to the Simple Object Access Protocol (SOAP) and travel over HTTP (over the public Internet), FTP, or any other reliable transport mechanism (such as IBM® MQSeries® technologies and CORBA, for transport over an enterprise intranet) may be used. Any application or functionality described herein may be implemented as native code, by providing hooks into another application, by facilitating use of the mechanism as a plug-in, by linking to the mechanism, and the like.

Exemplary networks may operate with any of a number of protocols, such as Internet protocol (IP), asynchronous transfer mode (ATM), and/or synchronous optical network (SONET), user datagram protocol (UDP), IEEE 802.x, etc.

Embodiments of the present invention may include apparatuses for performing the operations disclosed herein. An apparatus may be specially constructed for the desired purposes, or it may comprise a general-purpose device selectively activated or reconfigured by a program stored in the device.

Embodiments of the invention may also be implemented in one or a combination of hardware, firmware, and software. They may be implemented as instructions stored on a machine-readable medium, which may be read and executed by a computing platform to perform the operations described herein.

More specifically, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

In the following description and claims, the terms "computer program medium" and "computer readable medium" may be used to generally refer to media such as, but not limited to, removable storage drives, a hard disk installed in hard disk drive, and the like. These computer program products may provide software to a computer system. Embodiments of the invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Additionally, the phrase "configured to" or "operable for" can include generic structure (e.g., generic circuitry) that is manipulated by software and/or firmware (e.g., an FPGA or a general-purpose processor executing software) to operate in a manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

While a non-transitory computer readable medium includes, but is not limited to, a hard drive, compact disc, flash memory, volatile memory, random access memory, magnetic memory, optical memory, semiconductor based memory, phase change memory, optical memory, periodically refreshed memory, and the like; the non-transitory computer readable medium, however, does not include a pure transitory signal per se; i.e., where the medium itself is transitory.

Introduction

Background

"Enumerating molecules is a mind-boggling problem that has fascinated chemists and mathematicians alike for more than a century. Taking the definition from various dictionaries, to enumerate means (1) "to name things separately, one by one", and (2) "to determine the number of, to count." Interestingly enough, both definitions have been taken when enumerating molecules. Historically, the latter definition was first used, and mathematical solutions were devised to count molecules. Some of the solutions developed were not only valuable to chemists but to mathematicians as well. Indeed, as we shall see in this chapter, while trying to solve the problem of counting the isomers of paraffin structures' or counting substituted aromatic compounds, important concepts in graph theory and combinatorics were developed. The terms graph and tree were even coined in a chemistry context.

About four decades ago, with the advance of computer science, researchers started to look at the former definition of enumeration, and devised computer codes to explicitly list molecules. Again, while studying this challenging problem, important concepts in computer science were developed. Artificial intelligence textbooks generally quote DENDRAL, a code to enumerate molecules, as the first expert system. Historically, molecular enumeration has brought a fertile ground of research between chemistry, mathematics, and computer science. Still today new concepts and techniques are being developed at the interstice of these fields.

Enumerating molecules is not only an interesting academic exercise but has practical applications as well. The foremost application of enumeration is structure elucidation. Ideally, the . . . chemist collects experimental data (NMR, MS, IR, . . . ) for an unknown compound, the data is fed to a code, and the resulting unique structure is given back. Although such a streamlined picture is not yet fully automated, and may never be, there are commercial codes that can, for instance, list all structures matching a given molecular formula, an IR spectrum, or an NMR spectrum. Another important application is in molecular design. Here the problem is to design compounds (drugs, for example) that optimize some physical, chemical, or biological property or activity. Although not as prolific as structure elucidation, molecular design has introduced some novel stochastic solutions to molecular enumeration. Finally, with the advent of combinatorial chemistry, molecular enumeration takes a central role as it allows computational chemists to construct virtual libraries, test hypotheses, and provide guidance to design optimal combinatorial experiments." [Source: https://prod-ng.sandia.gov/techlib-noauth/access-control.cgi/2004/040960.pdf; retrieved on: Aug. 6, 2019].

"The term enumerating has been used in the literature for both listing molecules one by one and determining the number of molecules corresponding to a given set of constraints." [Source: https://prod-ng.sandia.gov/techlib-noauth/access-control.cgi/2004/040960.pdf; retrieved on: Aug. 6, 2019].

A Simple Graph

FIG. 1A illustrates multiple graphs 100A, including: a simple graph 102A, a multigraph 104A, and a molecular graph 106A, respectively, in accordance with an embodiment of the present invention. "A simple graph G is defined as an ordered pair G=(V(G),E(G)), where V=V(G) is a nonempty set of elements called vertices, and E=E(G) is a set of unordered pairs of distinct element of V called edges. In most cases of chemical interest[,] the sets V and E are finite . . . . Of course, there is a relationship between graphs and chemical structures . . . . [Simple graph 102A] can, for instance, be viewed as a representation of cyclohexane. But there are molecules that do not fit the simple graph picture. A multigraph is a graph where the edge set is not necessarily composed of distinct pair of vertices, in other words, multiple edges are allowed in a multigraph. A multigraph is without a loop when vertices are not allowed to be paired with themselves. [Multigraph 104A] is a representation of benzene. In a simple graph or a multigraph, the degree of a vertex is the number of edges attached to it, and the multiplicity of an edge is the number of times that edge occur in the graph . . . . [Simple graph 102A] contains vertices of degree 1 and 4, and all edges have multiplicity 1; in [multigraph 104A] the vertices have degrees 1 and 4 and the edges have multiplicities 1 and 2. The degree sequence of a graph or a multigraph is the sequence of numbers of vertices having a given degree starting with degree 0 and ending with the maximum degree for all vertices . . . . [Simple graph 102A] has no vertices of degree 0, 12 vertices of degree 1, no vertices of degree 2 and degree 3, and 6 vertices of degree 4, the degree sequence is (0,12,0,0,6). Graph (b) has the degree sequence (0,6,0,0,6)." [Source: https://prod-ng.sandia.gov/techlib-noauth/access-control.cgi/2004/040960.pdf; retrieved on: Aug. 6, 2019].

"While [multigraph 104A] could correspond uniquely to benzene, one cannot distinguish 1,2-dichlorobenzene from 1,4-dichlorobenzene using this representation. To make the distinction between the two compounds one has to attach to each vertex, a label, or color, that is unique to each element of the periodic table (for instance, the atomic symbol). Finally, in a molecular structure, atoms are always connected through some bonds, in other words, a molecular structure is in one piece. A molecular graph is thus defined as a connected multigraph with vertices colored by the atomic symbols of the periodic table. We use the term color instead of label since, as we shall see next, labeled graphs have a specific definition in graph theory. [Molecular graph 106A] is the molecular graph of 1,2-dichlorobenzene. Clearly, in a molecular graph, each vertex is an atom and each edge is a bond. The terms atom valence replace the terms vertex degree, and bond order replace edge multiplicity. Note that with the exception of rare gases, a molecular graph comprises more than one atom. Because molecular graphs are connected, their valence sequences start with valence 1 and usually end with valences 4 or 5 for most organic compounds. The valence sequence of benzene is (6,0,0,6)." [Source: https://prod-ng.sandia.gov/techlib-noauth/access-control.cgi/2004/040960.pdf; retrieved on: Aug. 6, 2019].

Building upon the general framework described above regarding identifying and numerically quantifying chemical structures and molecules as "graphs" suitable for subsequent calculation and manipulation, a multitude of theories and computational processes exist for the navigation of chemical space and location of individual searched-for chemical species and/or entities. Such efforts attempt to meet sizable industry demand in the area, provided that there is a need to: (1) characterize vast chemical space; and, (2) conveniently and reliably navigate chemical space. For instance, such problems, prior to the advent of sophisticated and powerful modern computers, appeared entirely intractable, e.g., the chemical space for (an enzyme for) benzene is two raised to power 6,441 possible isomers of 114 atoms from C, H, N, O.

It is understood that the development of pharmaceutical drugs, products, therapies and/or the like may cost upwards millions or even several billions of dollars. Effective computer-implemented computational and/or combinatorial tools and methods can open new territory through direct exploration of chemical space for new drug discovery and associated lead generation. More particularly, proprietary algorithms provided by the disclosed embodiments may also indicate exactly how many leads may need to be searched to return usable results for a particular project.

As commonly known, benzene is a substance known to be a carcinogen, which increases the risk of cancer and other illnesses, and is also a notorious cause of bone marrow failure. To better characterize, understand, account for, treat and/or cure illnesses caused by benzene and other carcinogens, it may be necessary to deconstruct a complex molecule, such as benzene, into its constituent elements using enzymes like an amino acid or proteins made from amino acids. Should such constituent substances fail to occur in nature, a search for an amino acid may involve hundreds of millions of isomers to computationally and/or combinatorically enumerate.

Treatments and therapies for cancer include chemotherapy and radiation therapy, with significant percentages of sufferers not surviving regardless of receiving such treatment, no available permanent cure, and very severe side effects. Similarly, regarding challenges faced due to inadequacies of currently available medical care, shortcomings in current industrial safety measures have left substantial numbers of people in certain industries facing the effects of exposure to various deleterious substances such as benzene.

Nevertheless, advances in current computer capabilities have produced favorable results regarding the reduction of vast numbers of isomers to molecular formulas. For example, a search executed via the disclosed embodiments for benzene results in 37 target formulas, 406 enzyme formulas and 37 analogs, and a unique dipeptide. Thus, successful and timely navigation of the once intractable and perpetual chemical space now appears possible and is outlined by the presented embodiments.

General Description of the Disclosed Embodiments

To create a computational and combinatorial computer-based algorithmic method to effectively navigate chemical space, e.g., as generally understood and defined herein as a concept in cheminformatics referring to the property space spanned by all possible molecules and chemical compounds adhering to a given set of construction principles and boundary conditions, thousands of chemical formulas were collected, including everything from molecules in air, food additives, alcohols, substances thought to cause cancer in rats and mice, in monkeys, vitamins, sugars, antibiotics, cancer markers, the stuff in DNA, chemotherapy drugs, cholesterol molecules, hemoglobin, coffee. Elements considered include that shown in the periodic table, commonly understood and defined herein to be a tabular display of the chemical elements, which are arranged by atomic number, electron configuration, and recurring chemical properties. The periodic table is ordered by atomic number, which may a special case of an integer called the index, e.g., as may be defined for a subset of the periodic table. The periodic table, as modeled and searched through herein, may be divided into two contiguous parts, and extended into a larger table with molecular formulas ordered by the index, which may have a constraint that forces the periodic table and/or elements and/or chemical structures associated therewith to change in discrete operations or steps.

Disclosed embodiments herein relate to the input of a chemical formula in a defined search space to obtain a list of chemical formulas that may bind or complex with the input formula.

Additional functionality of the disclosed embodiments include: to input one chemical formula and a byproduct formula and a search space to thus obtain a list of chemical formulas that might dissociate the byproduct from the input formula by way of catalysis; to input one chemical formula and a search space to obtain a list of chemical formulas that might be targets of that formula; to input one chemical formula and a search space to thus obtain a list of chemical formulas that might competitively inhibit that formula; to restrict the search results to particular sometimes unique dipeptides; to use these dipeptides to fingerprint a protein from its peptide sequence, and to search a protein database or use experimental methods to search for such proteins; to use above searches twice to obtain a list of formulas, amino acids or proteins that may cause drug resistance, or be markers of drug resistance; and, to perform multiple searches, build graphs or chains of interactions. Such a systematic computational and combinatorial computer-based algorithmic approach as disclosed herein successfully finds a needle, e.g., a desired target molecule, chemical structure, analog, moiety and/or the like, in a haystack of incomprehensible size, e.g., chemical space overall. Thus, disclosed systems and methods provide a powerful tool against every kind of disease or malfunction of very complex biochemical organisms.

System Structure

FIG. 1A illustrates a simple graph, a multigraph, and a molecular graph, respectively, in accordance with an embodiment of the present invention. In the present embodiment, simple graph 102A, multigraph 104A, and molecular graph 106A, respectively, are shown as a part of multiple graphs 100A, all of cyclohexane. By way of example and not limitation, in one of embodiments, multiple graphs 100A provide the foundation upon which any one or more of the below-disclosed computational and/or combinatorial algorithms may be based, e.g., such that the disclosed algorithms may receive such a structure as any one or more of multiple graphs 100A to enumerate the same for subsequent search purposes as may be necessary to locate related molecules, chemical structures and/or the like.

Figure 1B:
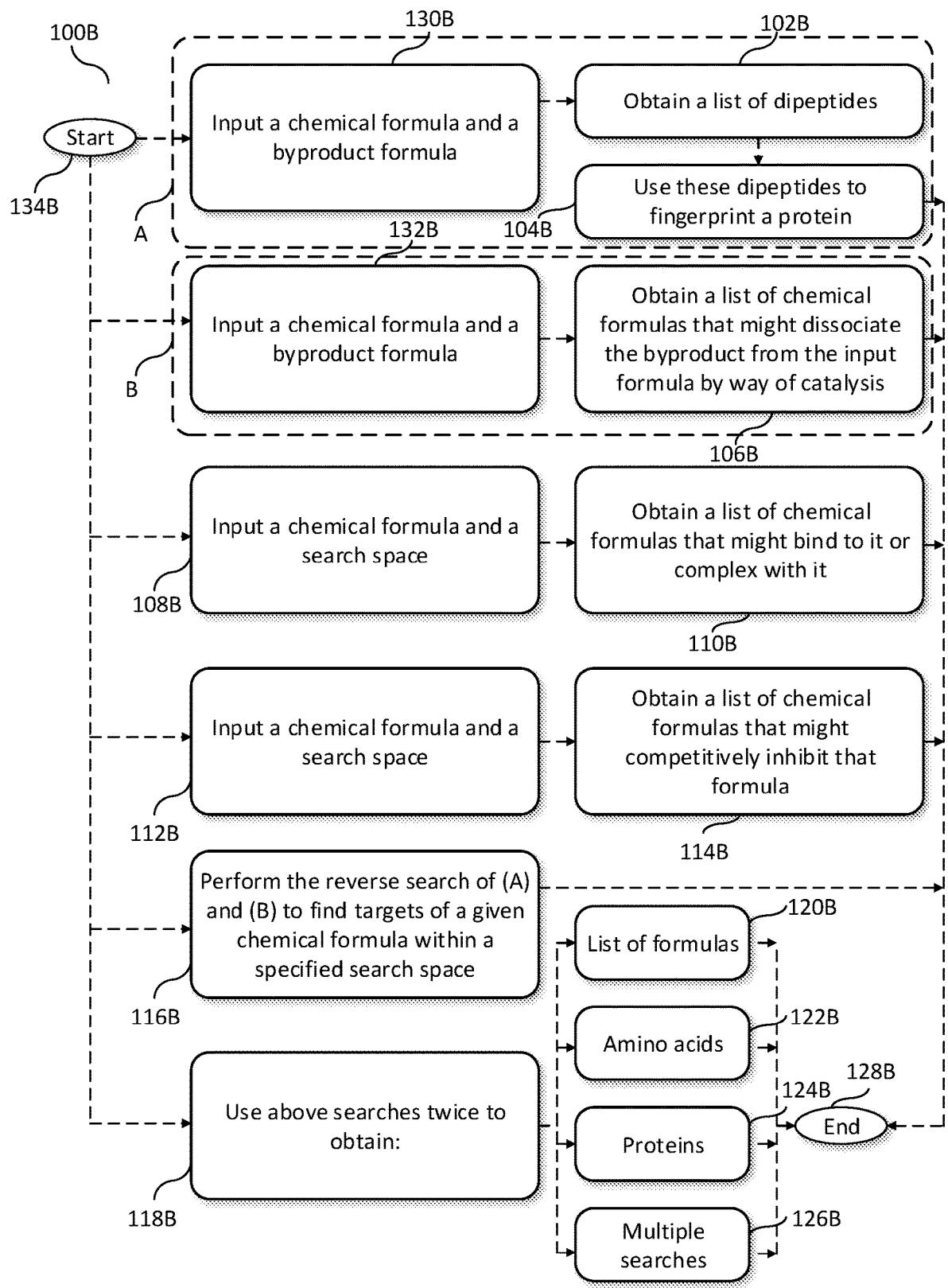
FIG. 1B illustrates a flowchart of an exemplary method of inputting a chemical formula and/or a byproduct formula to obtain a desired list of outcomes, e.g., including related formulas, amino acids, proteins, and/or further direction concerning multiple additional related searches and so on and so forth, in accordance with an embodiment of the present invention.

FIG. 1B illustrates a flowchart of an exemplary method of inputting a chemical formula and/or a byproduct formula to obtain a desired list of outcomes, e.g., including related formulas, amino acids, proteins, and/or further direction concerning multiple additional related searches and so on and so forth, in accordance with an embodiment of the present invention. In the present embodiment, a method 100B is shown that is at least partially implemented in a computer and executed by one or more processors associated therewith. Method 100B includes various routes, operations, steps, and/or sequences, etc., for outputting a number of related items, e.g., a list of formulas 120B, amino acids 122B, proteins 124B and/or additional sequential and/or concurrent searches 126B upon activation at a start operation 134B followed by, for example, any one or more of input operations 130B, 132B, 108B, and/or 112B, e.g., input a chemical formula and a byproduct formula operation 130B. In an alternative embodiment shown in 508 a chemical formula includes predefined elements such as, without limitation, letter sequences made of G A S P V T C N D I L E Q M K H F R V W, assuming the user provides an assumed index to each such as, without limitation, G 40, A 48, S 56 etc, and a valence to each such as, without limitation, 2. A search space may, without limitation, also include such predefined elements.

By way of example and not limitation, following route "A' of method 100B, input of chemical formula and a byproduct formula operation 130B yields obtain a list of dipeptides operation 102B. A dipeptide, as commonly understood and defined herein, refer to an organic compound derived from two amino acids. The constituent amino acids can be the same or different. When different, two isomers of the dipeptide are possible, depending on the sequence. Several dipeptides are physiologically important, and some are both physiologically and commercially significant. A well-known dipeptide is aspartame, an artificial sweetener. Such dipeptides may then be used at use these dipeptides to fingerprint a protein operation 104B to fingerprint a protein prior to conclusion of method 100B at end operation 128B.

By way of example and not limitation, following route "B" of method 100B, input of chemical formula and a byproduct formula operation 132B yields obtain a list of chemical formulas that might dissociate the byproduct from the input formula by way of catalysis operation 106B prior to conclusion at end operation 128B. Alternatives to routes "A" and "B" as shown in FIG. 1B and described herein, include the following: input a chemical formula and a search space operation 108B that yields an obtain a list of chemical formulas that might bind or complex with the input chemical formula operation 110B; input a chemical formula and a search space operation 112B that yields an obtain a list of chemical formulas that might competitively inhibit the input chemical formula operation 114B; or a perform the reverse search of "A" and "B" to find targets of a given chemical formula within a specified search space, all prior to end operation 128B to conclude method 100B. Additionally, or in the alternative to any one or more that described above, any one or more of the operations may be repeated by use above searches twice module or operation 118B to yield any one or more of a list of formulas 120B, amino acids 122B, proteins 124B and/or additional sequential and/or concurrent searches 126B prior to end operation 128B. Those skilled in the art will appreciate the type, configuration, placement and/or order, etc., of the various modules and/or operations shown in FIG. 1B are by way of example only and thus not limiting to that shown. Other suitable type, configuration, placement and/or orders may exist without departing from the scope and spirit of the disclosed embodiments.

Figure 2:
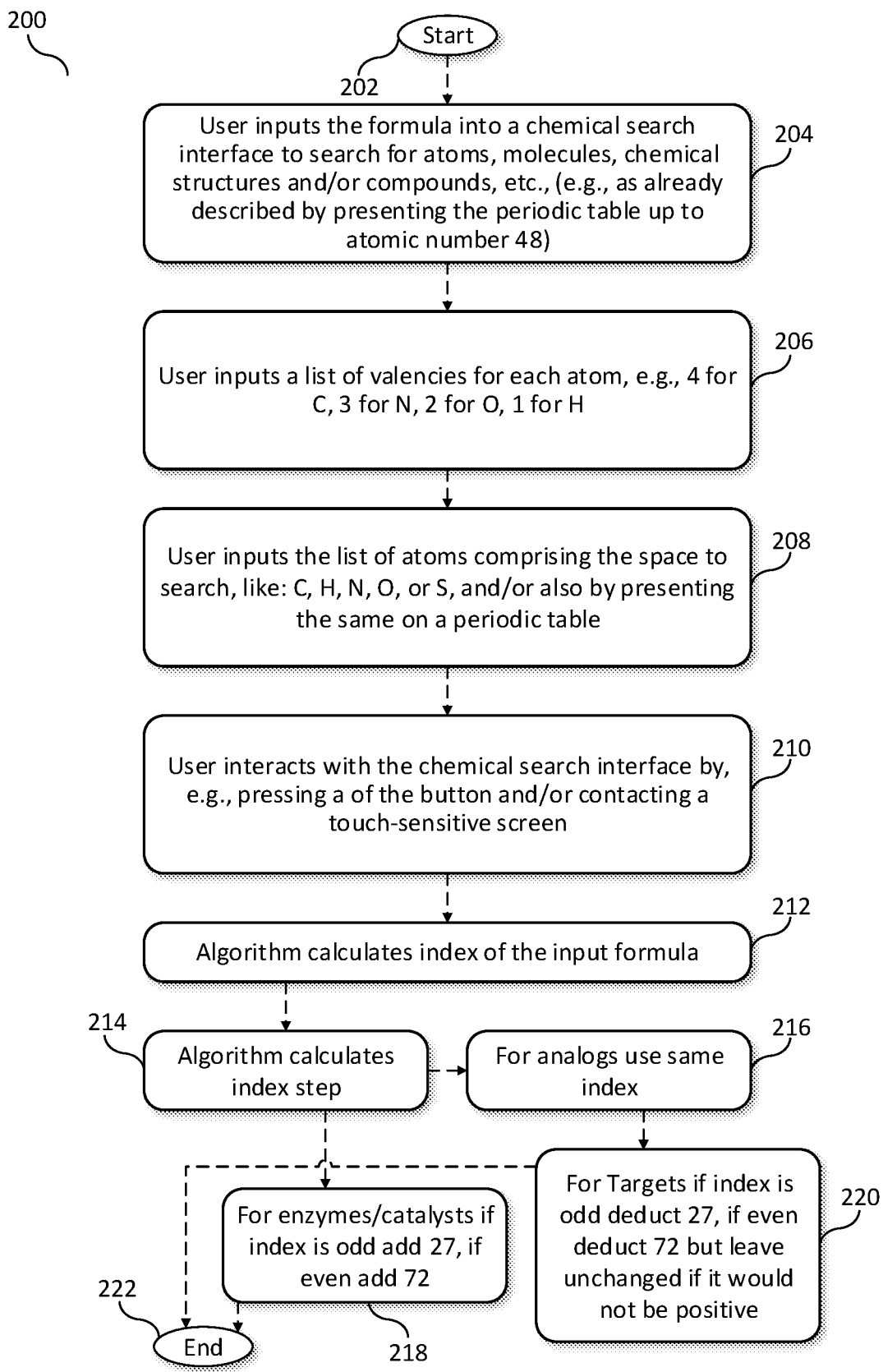
FIG. 2 illustrates a flowchart of an exemplary method of inputting a formula into a chemical search interface to search for atoms, molecules, chemical structures and/or compounds, etc., to calculate an index of the input formula, in accordance with an embodiment of the present invention.

FIG. 2 illustrates a flowchart of an exemplary method of inputting a formula into a chemical search interface to search for atoms, molecules, chemical structures and/or compounds, etc., to calculate an index of the input formula, in accordance with an embodiment of the present invention. In the present embodiment, general background information necessary for the performance of method 200 includes reference to a particular input molecular formula or isomer as being identified as "consistent" if its index, e.g., as calculated through any known method and/or by proprietary algorithms associated with the presently disclosed embodiments such as being proportionate to the number of valencies of a given element and/or compound, is not divisible by 3, and "inconsistent" if its index is a multiple of 3. Further, small molecules may avoid inconsistency by becoming ions or even adopting open shell configuration.

By way of example and not limitation, method 200 may begin at start operation 202 where, subsequently, a user of method 200, e.g., at least partially implemented in a computer, inputs the formula into a chemical search interface to search for atoms, molecules, chemical structures and/or compounds, etc., (e.g., as already described by presenting the periodic table up to atomic number 48) at chemical formula input operation 204. The user next inputs a list of valencies required for each atom, e.g., 4 for C, 3 for N, 2 for O, 1 for H, at valency input operation 206 prior to inputting the list of atoms comprising the space to search, like: C, H, N, O, or S, and/or also by presenting the same on a periodic table at chemical space definition input operation 208. The user may then next interact with the chemical search interface by, e.g., pressing a of the button and/or contacting a touch sensitive screen at interface interaction input operation 210 to trigger the chemical search interface to calculate, using one or more algorithms, an index of the input formula at index calculation operation 212 prior to any one or more of those algorithms being further used to calculate an index step at an index step calculation operation 214. In the example of dichlorobenzine at 202, without limitation, at 204 user inputs C6H4Cl2, at 208 user selects search space C_H_N_O_, at 210 user selects Enzymes, at 212 index 74 calculated by 6 multiplied by 6, added to 4 multiplied by 1, added to 2 multiplied by 17 prior to further steps Chemical structural analogs may, by way of example and not limitation, in one or more embodiments, use the index calculated in index calculation operation 212 at analog index usage operation 216, where method 200 may then proceed to numerical adjustment operation 220, where for certain enumerated chemical target formulas, if the calculated index is odd 27 is deducted therefrom, or, if even, 72 may be deducted therefrom, or—alternatively—the index may be left unchanged if doing so would yield a negative result.

Should knowledge of chemical structural analogs not be desired, method 200 may proceed to enzyme or catalyst adjustment operation 218, where, for enzymes/catalysts if the calculated index is odd 27 is added thereto, if even 72 is added thereto prior to conclusion of method 200 at end operation 222.

Figure 3:
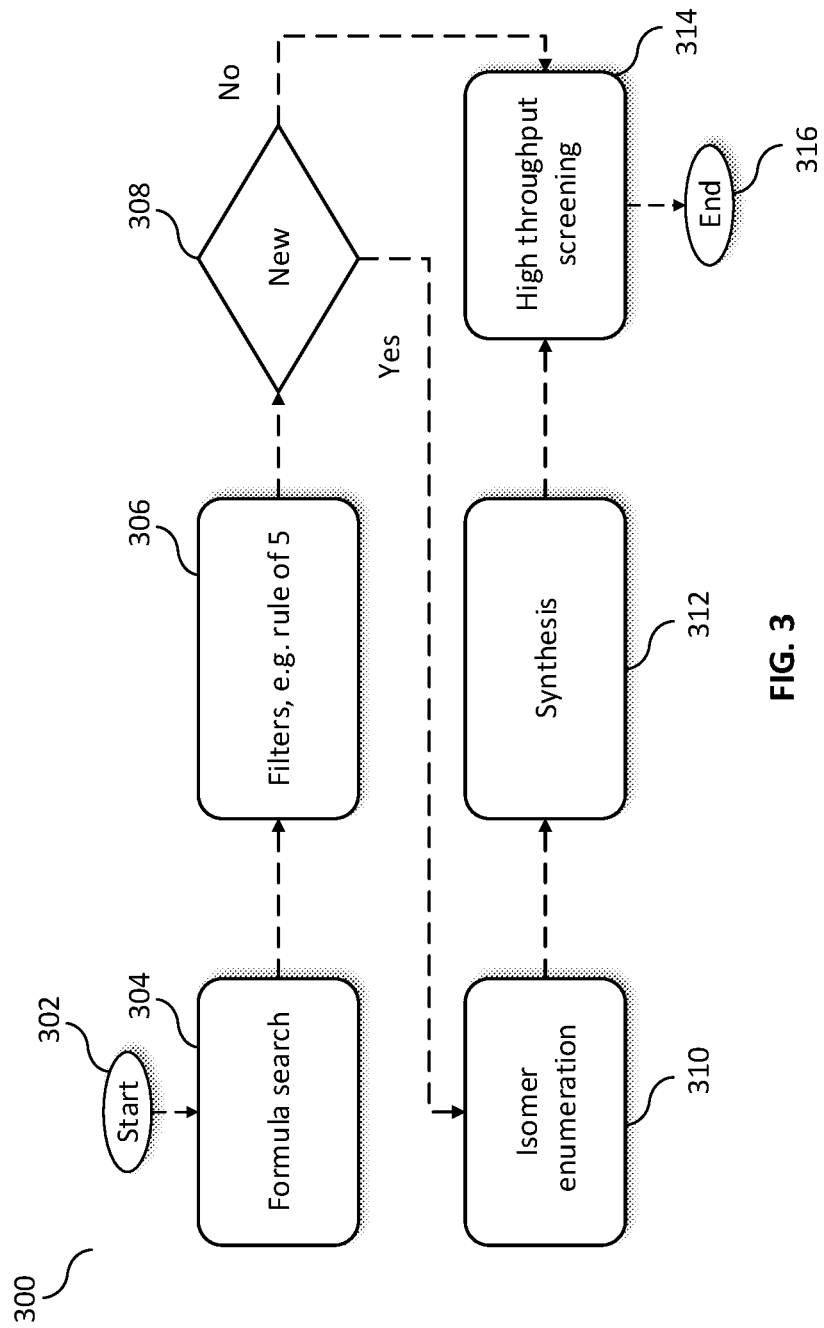
FIG. 3 illustrates a flowchart of an exemplary method of how to use a formula search for high throughput screening in accordance with an embodiment of the present invention.

FIG. 3 illustrates a flowchart of an exemplary method of how to use a formula search for high throughput screening in accordance with an embodiment of the present invention. In the present embodiment, method 300 is shown for conducting a high-throughput screening of chemical structures, compounds, and/or the like in accordance with any one or more of the algorithmic, computational and/or combinatorial procedures in accordance with the presently disclosed embodiments. By way of example and not limitation, method 300 may be a high-level and/or general representation of how to use any one or more of the searching, characterizing, navigating and/or parsing algorithms for traversing chemical space as disclosed herein.

Method 300 may begin at start operation 302 from which a formula search may be entered at a formula search entrance operation 304, whereupon such input formula and/or formulae may be subjected to one or more filters at filter operation 306, by way of example and not of limitation using Lipinski rule of five. Lipinski, C. A., Lombardo, F., Dominy, B. W., Feeney, P. J. (1997). Experimental and computational approaches to estimate solubility and permeability in drug discovery and development settings. Advanced Drug Delivery Reviews, 23, 3-25. Completion of application of filter operation 306 progresses method 300 to novelty determination operation 308, where the novelty of an input chemical formula and/or formulae is assessed.

An assessment of "yes" yields isomer enumeration operation 310 where any one or more or all isomers of a particular input chemical formula and/or formulae are assessed via traditional known chemical structure enumeration methods or those proprietary and associated with the presently disclosed embodiments prior to progressing to synthesis operation 312, where complete chemical reaction modeling may occur upon input of additional and/or different reagents intended to simulate a reaction with originally input chemical formula and/or formulae at formula search entrance operation 304 prior to progression to high throughput screening operation 314 and conclusion of method 300 at end operation 316.

Alternatively, an assessment of "no" at novelty determination operation 308 may progress method 300 directly to high throughput screening operation 314 and conclusion of method 300 at end operation 316. "High-throughput screening", as both generally understood and referred to herein, refers to and/or implies a method for scientific experimentation especially used in drug discovery and relevant to the fields of biology and chemistry. [Source: Inglese J and Auld D S. (2009) Application of High Throughput Screening (HTS) Techniques: Applications in Chemical Biology in Wiley Encyclopedia of Chemical Biology (Wiley & Sons, Inc., Hoboken, N.J.) Vol 2, pp 260-274 doi/10.1002/9780470048672.wecb223; Macarron, R.; Banks, M. N.; Bojanic, D.; Burns, D. J.; Cirovic, D. A.; Garyantes, T.; Green, D. V.; Hertzberg, R. P.; Janzen, W. P.; Paslay, J. W.; Schopfer, U.; Sittampalam, G. S. (2011). "Impact of high-throughput screening in biomedical research". Nat Rev Drug Discov. 10 (3): 188-195.] Using robotics, data processing/control software, liquid handling devices, and sensitive detectors, high-throughput screening allows a researcher to quickly conduct millions of chemical, genetic, or pharmacological tests. Through this process one can rapidly identify active compounds, antibodies, or genes that modulate a particular biomolecular pathway. The results of these experiments provide starting points for drug design and for understanding the noninteraction or role of a particular location.

Figure 4A:
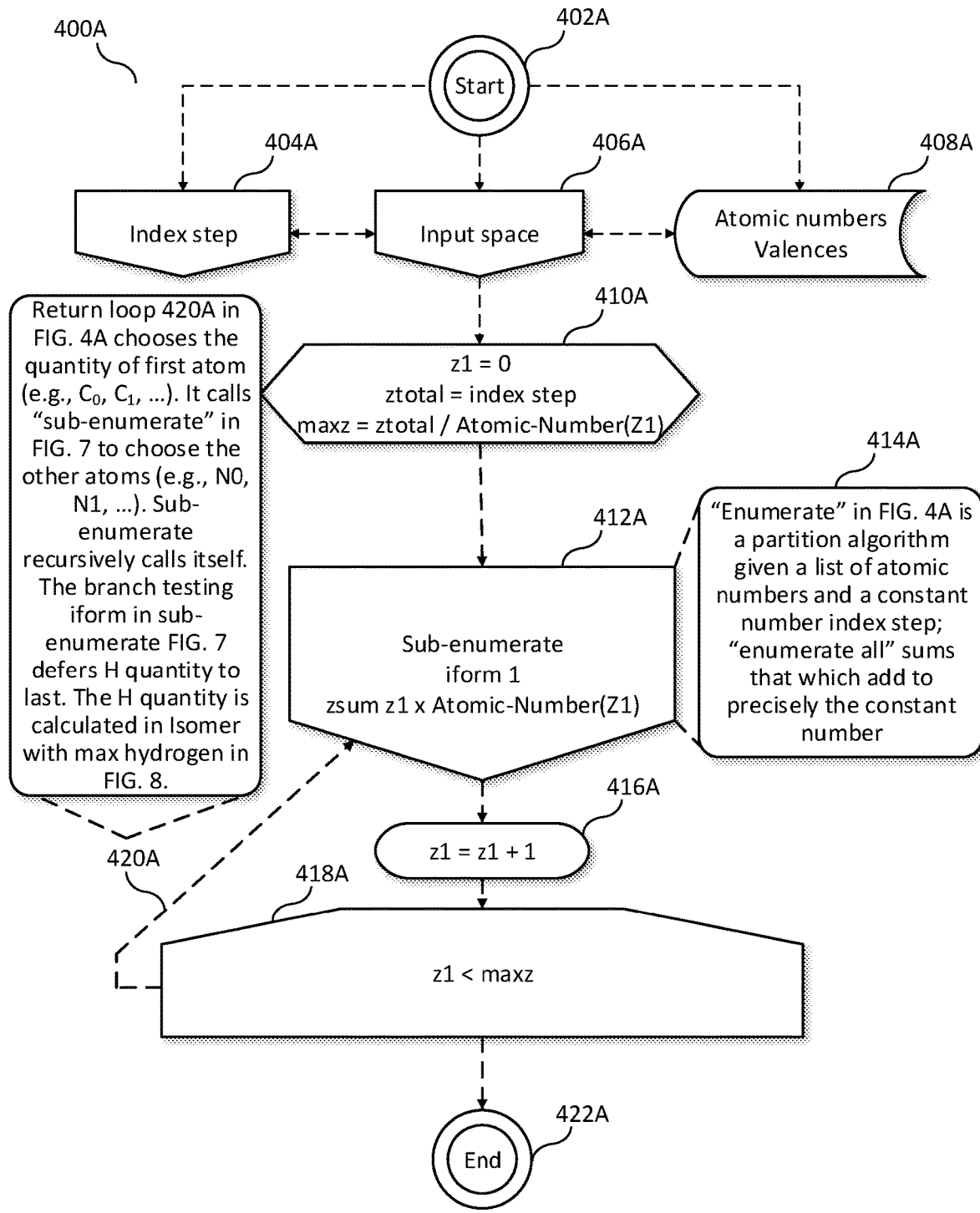
FIG. 4A illustrates a flowchart of an exemplary method of how to make a formula search for high throughput screening, in accordance with an embodiment of the present invention.

FIG. 4A illustrates a flowchart of an exemplary method of how to make a formula search for high throughput screening, in accordance with an embodiment of the present invention. In the present embodiment, method 400A begins at start operation 402A that may progress to any one or more or all of the following: index operation 404A, input space 406A, and atomic numbers and/or valences 408A. Index operation 404A may calculate and/or otherwise attribute an index value via isomer enumeration to one or more input chemical formulae into method 400A; likewise, input space 406A may be representative of the chemical space in which related chemical formulae, species, analogs, and/or the like are sought; and, atomic numbers and/or valences 408A may consider the atomic number and/or valency of input chemical formulae. By way of example, without limitation, method 410A initializes loop 412A to 420A. In method 410A ztotal is used to calculate maxz. Example dichlorobenzine index 74+step 72=byproduct index 12=index step 134; maxz is the most of 1st atom usually C, example dichlorobenzine maxz=134/6=22 which used as loop limit in 418A. It is not necessary to incrementally advance by sequential integer values. The order is not important, it can be in any order covering the same range.

By way of example and not limitation, in one or more embodiments, calculative methods associated with index operation 404A may calculate an index value for an input chemical structure and/or the like at start operation 402A by the following example algorithm: the atomic number of a given element, e.g., equivalent to the number of protons in the nucleus of the given atom and/or element such as 8 for oxygen ("O"), 1 for hydrogen ("H"), so on and so forth, added to any (absolute value of) number of additional electrons for a charged ion, e.g., an anion. Thus, in this context, an index value for an input formula of the hydroxide anion, e.g., $OH^-$, results in an index value calculation at index operation 404A as follows: (index value of O)+(index value of H)+(absolute value of any additional electrons)=8+1+1=10. Similarly, an index value calculated solely for the hydroxy group with the chemical formula of OH may be calculated by the index operation 404A as follows: (index value of O)+(index value of H)=8+1=9. Those skilled in the art will appreciate that the above-included examples of enumeration for calculating index values by operation 404A are provided for illustrative purposes only and that many other suitable alternative calculative procedures may be employed by index operation 404A without deviating from the scope and spirit of the presently disclosed embodiments.

Method 400A, after considering any one or more of index operation 404A, input space 406A, and atomic numbers and/or valences 408A may progress to increment operation 410A, which, as shown in FIG. 4A, may assign an initial increment start position or value of "0" to systematically cycle through index values associated with corresponding chemical structures and/or formulae to identify isomers and/or other compounds related to input chemical formulae. Such increment operation 410A may assign a total number of increments and/or steps equivalent to the index attributed to an input chemical formula and/or a maximum number of increments proportionate to a total value, e.g., "ztotal", divided by the atomic number of the input chemical formula.

Method 400A then progresses from increment operation 410A to enumerate and/or sub-enumerate operation 412A, which may involve a multiplication modification of incremented values associated with the index of an input chemical structure by its atomic number as shown in FIG. 4A and/or involve any other mathematical modification. By way of example and not limitation, enumerate related operations in FIG. 4A may be further explained in addendum 414A as a partition algorithm given a list of atomic numbers and a constant number index step. In an embodiment, "enumerate all" sums that which add to precisely a constant number; e.g., given C, H and 11 are an input list may be proportionate to each atoms respective atomic number, e.g., [6,1] and 11. Calculative procedures may include, in one or more embodiments, iteratively cycle through various additive combinations of C and H that can add up to a total of 11, e.g., C having an atomic number of 6, H having an atomic number of 1, and so on and so forth.

Completion of enumeration operations as described in connection with enumerate and/or sub-enumerate operation 412A may progress method 400A to subsequent increment operation 416A where the index step calculated earlier at increment operation 410A, for example, or any operation thereafter, may be again incremented to approach a max iteration value "maxz" at iteration maximum identification operation 418A.

Method 400A here may return via return loop 420A to enumerate and/or sub-enumerate operation 412A in some embodiments. More particularly, by way of example and not limitation, return loop 420A in FIG. 4A chooses the quantity of first atom (e.g., C0, C1, . . . ) to then call enumerate and/or sub-enumerate operation 412A, e.g., further shown as "sub-enumerate" in FIG. 7, to choose the other atoms (e.g., $N_0$, $N_1$, . . . ). In some embodiments, enumerate and/or sub-enumerate operation 412A recursively calls itself. In certain embodiments, branch testing "iform" in sub-enumerate FIG. 7 defers H quantity to last. In other embodiments, the H quantity may be calculated for one or more isomers with max hydrogen in FIG. 9. Method 400A may conclude should a satisfactory number of iterations be completed yielding index values (e.g., denoted by "z") being less than a max index and/or iteration value "maxz" at end operation 422A. An aspect of method 400A is to produce the requested list of molecular formulas and show how many there could be.

Figure 4B:
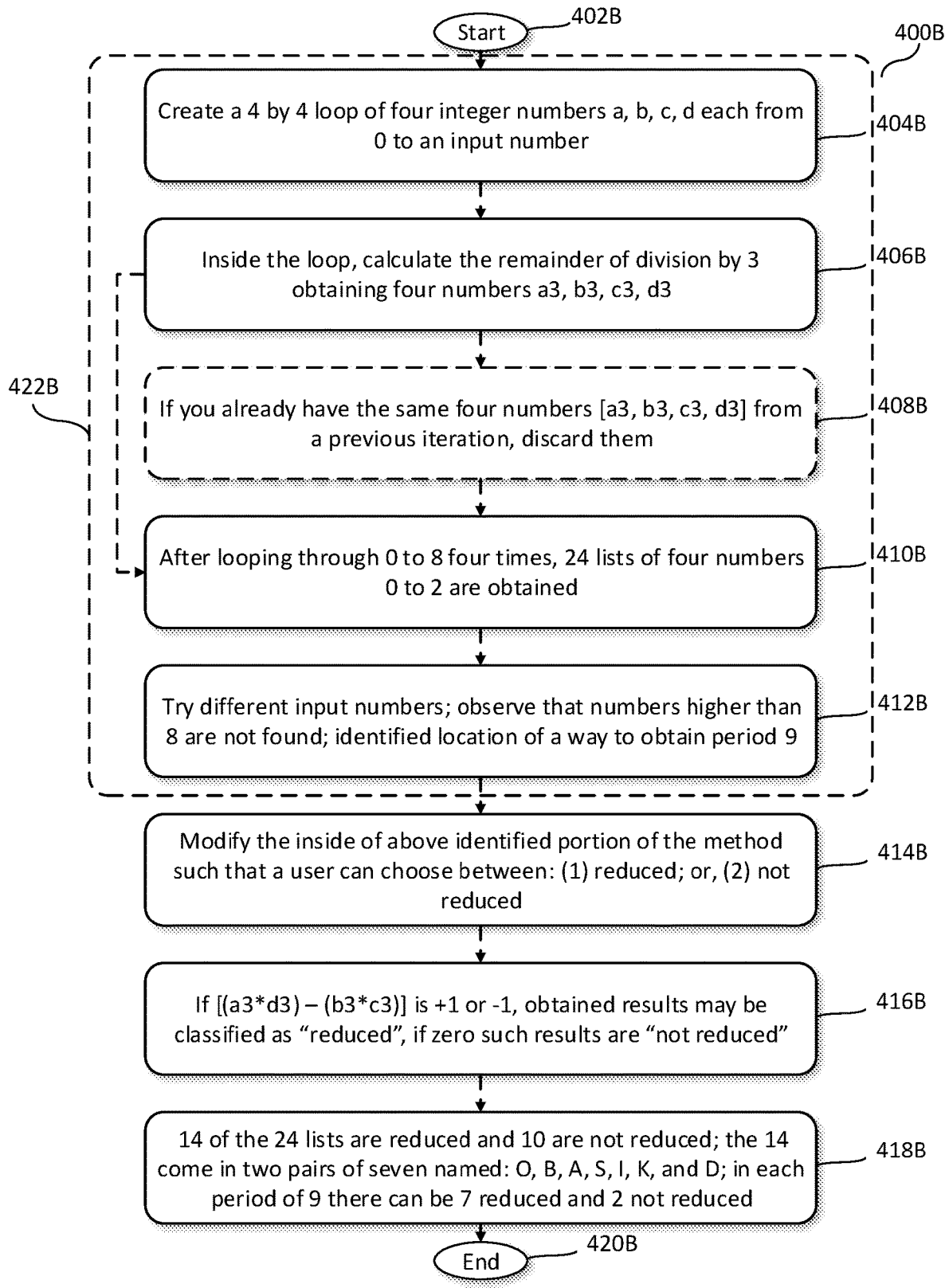
FIG. 4B illustrates a flowchart of an exemplary method of how to make a computational and/or combinatorial algorithm for that shown in FIG. 4A, in accordance with an embodiment of the present invention.

FIG. 4B illustrates a flowchart of an exemplary method of how to make a computational and/or combinatorial algorithm for that shown in FIG. 4A, in accordance with an embodiment of the present invention. In the present embodiment, a 4-by-4 loop is defined as a for loop for d within a for loop for c within a for loop for b within a for loop for a. In the present embodiment, method 400B begins at start operation 402B from which a 4-by-4 loop is created of four integer numbers a, b, c, d each from 0 to an input number at operation 404b, where (inside the loop) a calculation of a division of the four integer numbers a, b, c, d by 3 is performed to obtain four numbers a3, b3, c3, d3 at operation 406B. Should such numbers calculated at operation 406B equal those obtained from a previous iteration of operation 406B, such numbers may be discarded at operation 408B. After looping through 0 through an example input number of 8 four times, in one or more embodiments, 24 lists of four numbers including representative numbers 0 and 2 may be obtained at operation 410B. In this manner, at least for the present embodiment, 24 spin up states and 24 spin down states have the same period 9 as found in the periodic table.

Next, at operation 412B, different input numbers, e.g., for input as an input number at operation 404B, may be tried to, for example (but not limitation), observe that numbers higher than 8 are not found and/or to identify location of atoms and/or moieties to obtain calculative identification of atoms of a certain specific period, e.g., period 9. By way of example and not limitation, in one or more embodiments, operations 404B-412B may be collectively referred to as group operation 422B.

Subsequent to successful completion of group operation 422B, method 400B may proceed to operation 414B where any one or more operations identified within the inside of group operation 422B of method 400B can permit a user of the same to choose between: (1) reduced; or, (2) not reduced states and/or conditions. Operation 416B later determines, by way of example and not limitation, if [(a3*d3)−(b3*c3)] is +1 or −1, obtained results may be classified as "reduced", if zero such results are "not reduced" before operation 418B that may find that 14 of the 24 lists of four numbers from operation 410B may be reduced and 10 may not be reduced; the 14 come in two pairs of seven named: O, B, A, S, I, K, and D; in each period of 9 there can be 7 reduced and 2 not reduced prior to conclusion of method 400B at end operation 420B.

Figure 4C:
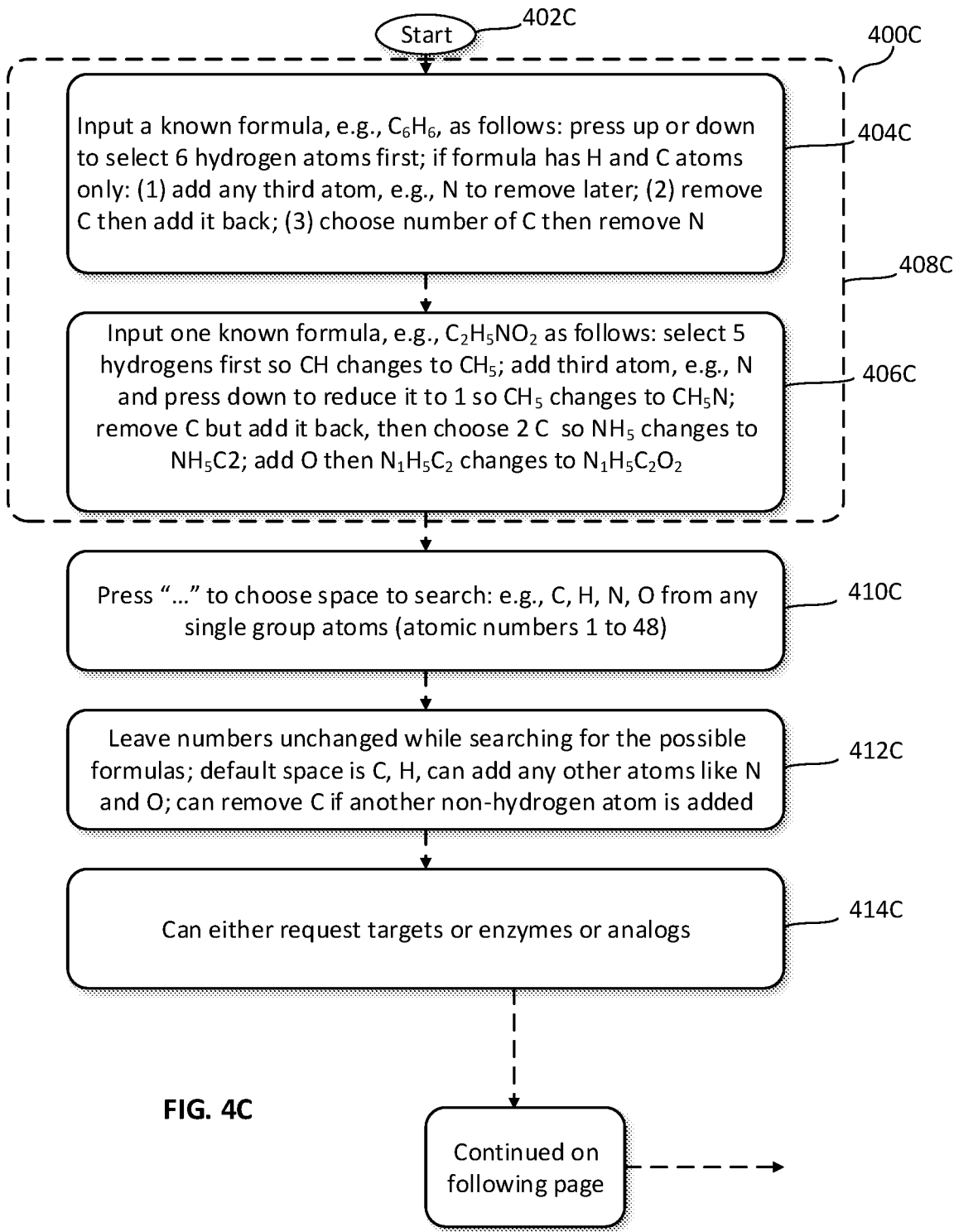
FIG. 4C illustrates a flowchart of an exemplary method of how a pharmaceutical company or other interested party and/or entity may use the computational and/or combinatorial algorithm shown in FIG. 4B, in accordance with an embodiment of the present invention.
Figure 4C:
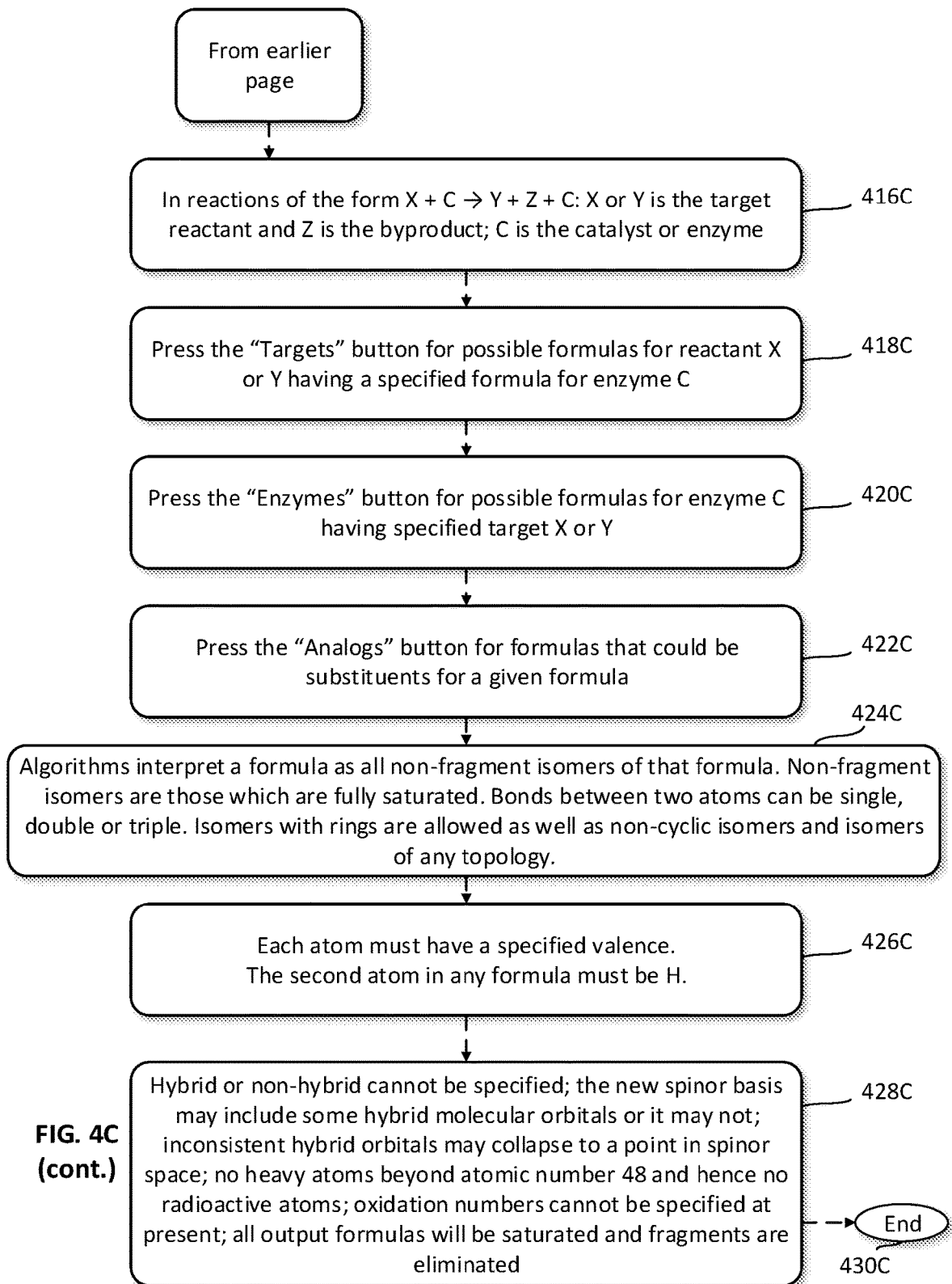

FIG. 4C illustrates a flowchart of an exemplary method of how a pharmaceutical company or other interested party and/or entity may use the computational and/or combinatorial algorithm shown in at least FIG. 4B, in accordance with an embodiment of the present invention. In the present embodiment, any one or more of the systems, methods, and/or search algorithms presented in the preceding figures and described in connection therewith may be adapted, adjusted or otherwise used by a search entity such as a pharmaceutical company through method 400C which may begin at start operation 402C. Input of a known formula, e.g., $C_6H_6$, may occur, e.g., through input by a user of method 400C, at input operation 404C as follows: press up or down to select 6 hydrogen atoms first; if formula has H and C atoms only: (1) add any third atom, e.g., N to remove later; (2) remove C then add it back; (3) choose number of C then remove N. Next, at operation 406C, input of other known formulas, e.g., $C_2H_5NO_2$ may occur as follows: select 5 hydrogens first so CH changes to $CH_5$; add third atom, e.g., N and press down to reduce it to 1 so $CH_5$ changes to $CH_5N$; remove C but add it back, then choose 2 C so $NH_5$ changes to $NH_5C2$; add O then $N_1H_5C_2$ changes to $N_1H_5C_2O_2$. Those skilled in the art will appreciate that operations 404C and 406C may be collectively referred to as group operation 408C and include additional or fewer chemical structure and/or formula input operations other than that shown in method 400C of FIG. 4C without departing from the scope and spirit of the presently disclosed embodiments. Subsequent to group operation 408C, a user of method 400C may press, e.g., on an appropriately equipped at least partially computer-based interface, an identified key and/or key strokes such as " . . . " to choose the particular desired chemical space to search: e.g., C, H, N, O from any single group atoms (atomic numbers 1 to 48). Default settings, e.g., regarding searching for chemical formulas related to an input formula input at group operation 408C, may be input at operation 412C, e.g., where numbers of single group atoms input earlier at operation 410C may be left unchanged while searching for possible related chemical formulas; default space is C, H, can add any other atoms like N and O; and, it may be possible for the removal of C if another non-hydrogen atom is added. At operation 414C, the user may request target compounds and/or formulas, enzymes, and/or chemical analogs as those sought to appear within any results, etc.

Next, at operation 416C, reactions may be searched for where such reactions may generally be input or viewed in the form X+C→Y+Z+C, where X or Y is the target reactant and Z is the byproduct, and C is the catalyst or enzyme. By way of example and not limitation, in one or more embodiments, a user may be enabled to press a button denoted as "targets" for possible formulas for a given input reactant X or Y having specified formula for an enzyme C at operation 418C. Likewise, such a user may be enabled at operation 420C to press an "enzymes" button to search for an uncover possible formulas for enzyme C having specified target X or Y; and, to press an "analogs" button, at operation 422C for formulas that could be substituents for a given formula.

Ongoing operation 424C indicates that algorithms associated with method 400C interpret a formula as, for example (but not limitation thereto), all non-fragment isomers of that formula. In an example, non-fragment isomers may be defined as those which are fully saturated. Bonds between two atoms can be single, double or triple. Isomers with rings are allowed as well as non-cyclic isomers and isomers of any topology. Ongoing operation 426C may indicate that input atoms must each have a specified valence, where the second atom in any formula must be H.

Operation 428C, which in some embodiments may be considered to be a "catch-all" type operation intended to encompass various specifics not set forth and discussed explicitly for method 400C, may at least include any one or more of the following conditions: hybrid or non-hybrid cannot be specified; a new spinor basis (e.g., for input chemical formulas) may include some hybrid molecular orbitals or it may not; inconsistent hybrid orbitals may collapse to a point in spinor space; no heavy atoms may be permitted or considered beyond atomic number 48 (e.g., hence no radioactive atoms); oxidation numbers cannot be specified at present; all output formulas may be saturated and fragments are eliminated. Method 400C may then culminate at end operation 430C. Those skilled in the art will appreciate the configuration possibilities set forth here are provided for example purposes only and that additional or fewer configurations may exist regarding manipulation and search for related chemical formulas relative to an input formula, inclusive of enzymes, etc., without departing from the scope and spirit of the disclosed embodiments.

Figure 5:
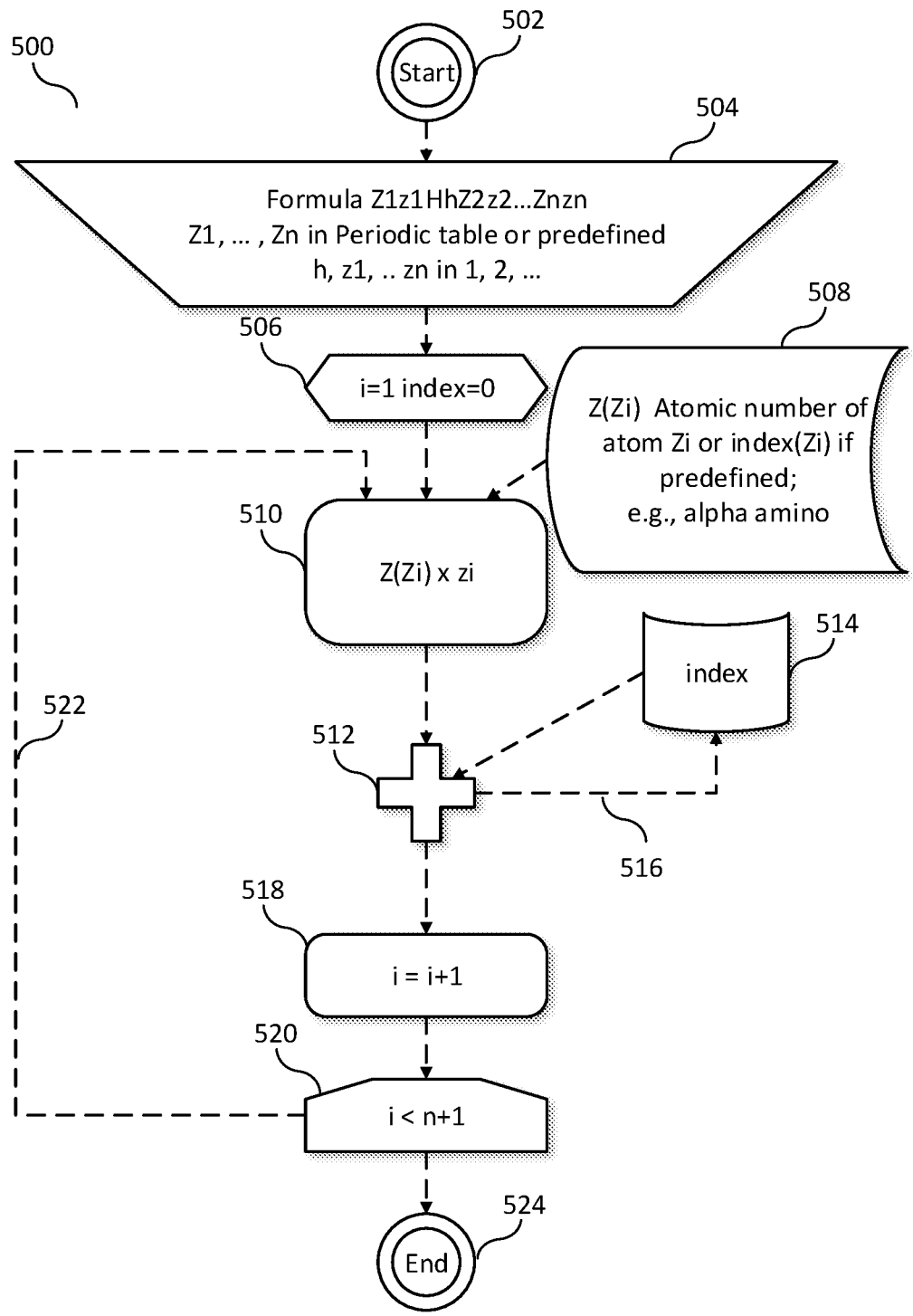
FIG. 5 illustrates a flowchart of an exemplary method of how to calculate an index for that shown in FIG. 3, in accordance with an embodiment of the present invention.

FIG. 5 illustrates a flowchart of an exemplary method of how to calculate an index for that shown in FIG. 3, in accordance with an embodiment of the present invention. In the present embodiment, method 500 to calculate an index numerical value may be performed at, for example, index operation 404A of method 400A shown in FIG. 4A and may begin at start operation 502. Next, at operation 504, chemical formulas may be input having a general format of, for example (but not limitation thereto): $Z1z1HhZ2z2\ldots Znzn$ and/or the like. Operation 506 may incrementally define or otherwise attribute index values to molecules and/or chemical structures in accordance with their respective atomic numbers and additions made to account for additional electrons prevalent in charged ions. Such calculative procedures are detailed for index operation 404A of method 400A shown in FIG. 4A and are not repeated herein. Indexing calculations, in one or more embodiments, may be calculated iteratively and thus have incremental index, or "i" values beginning from "0" and incrementing, by integer values, forward. The symbol Z is conventional for atomic number. Z1 is usually C, Z2 is always H so omitted, Z3 is often N. In method 508 $Z1, Z3 \ldots Zn$ could also be amino acids from G A S P V T C N D I L E Q M K H F R V W, and predefined or pre-calculated values like Z(G)=40, Z(A)=48, Z(S)=56 etc stored.

Operation 510 may be described by notation 508, which indicates that $Z(Zi)$ may represent the atomic number of a given atom Zi or calculated index(Zi) for a given chemical structure or formula, where such an atomic number or index value may be further numerically aggregated, multiplied or manipulated and/or incremented by addition operation 512 that may, in some embodiments, also incorporate an index operation 514 that may be iteratively repeated in loop 516 prior to increment operation 518. Assessment of increment value "i" at operation 520 permits for method 500 to conclude at end operation 524 should less than a specified total "n+1" value be attained by increment operation 518, or (alternatively) method 500 may return to operation 510 via loop operation 522. Thus, method 500 may be performed repeatedly to iteratively enumerate chemical structures of input formula and systematically identify and output relates formulas thereto dependent at least partially upon chemical formula input at start operation 502 and subsequent operations.

Figure 6:
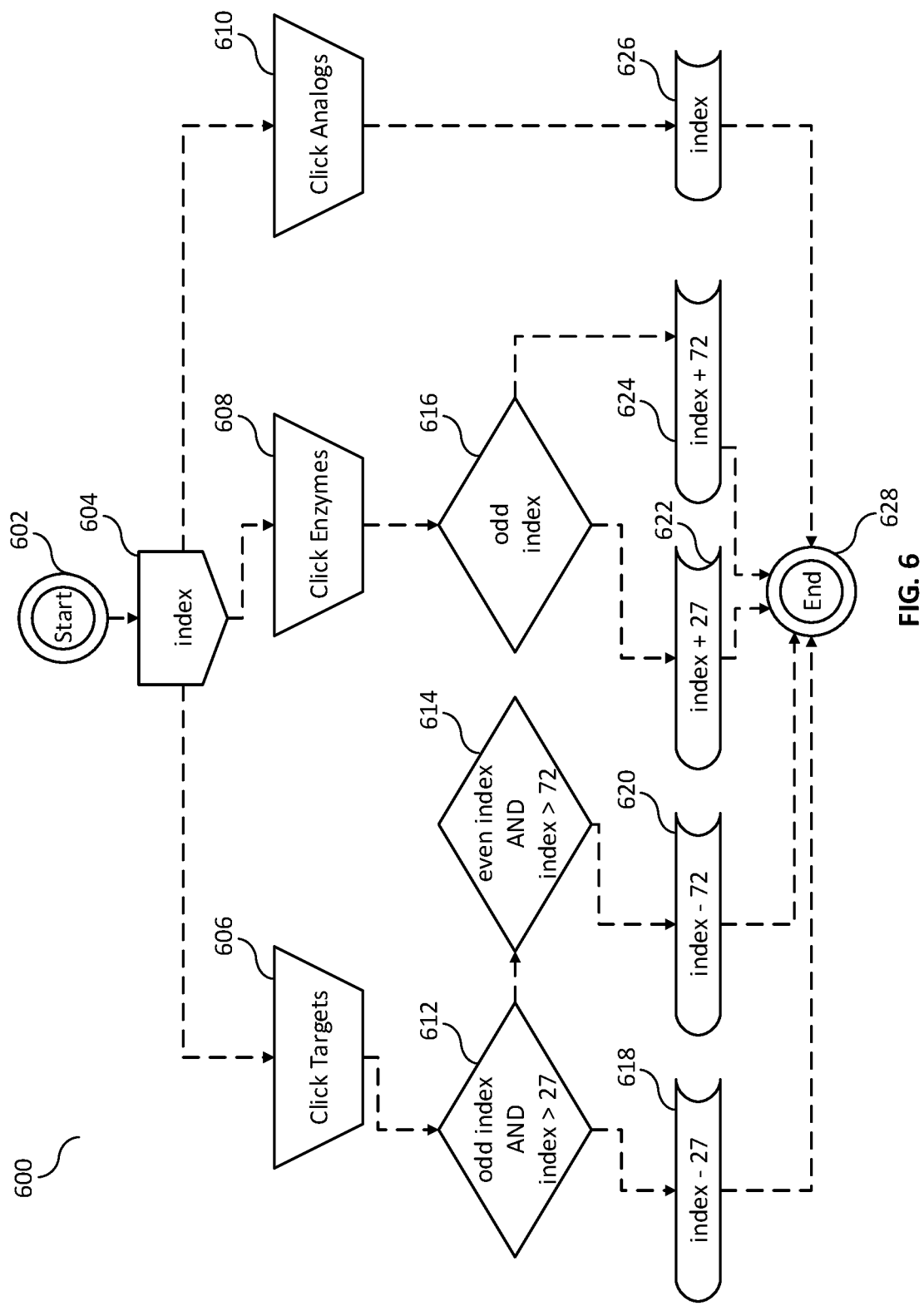
FIG. 6 illustrates a flowchart of an exemplary method of an index calculation operation, in accordance with an embodiment of the present invention.

FIG. 6 illustrates a flowchart of an exemplary method of an index calculation operation, in accordance with an embodiment of the present invention. In the present embodiment, method 600 to calculate an index for chemical formulas and/or structures input thereto may begin at start operation 602 that proceeds to index operation 604 that provides for user interactivity to engage, e.g., by clicking on or otherwise activating, search capabilities regarding the following: targets 606, enzymes 608, and analogs 610.

Index values intended to be calculated on behalf of targets 606, e.g., as may be determined by any one or more of the index value calculative methods previously presented and discussed, may be further augmented or numerically manipulated, e.g., for odd index values, at odd index value operation 612 that may progress method 600 subtraction operation 618 where 27 may be subtracted from the odd index calculated value at operation 612 prior to culmination of method 600 at end operation 628. Those skilled in the art will appreciate that the exact number values subtracted at subtraction operation 618 may be different than 27, e.g., higher or lower, depending on the calculative metric employed by method 600 without departing from the scope and spirit of the disclosed embodiments. An aspect of 27 and 72 and 11 is that they are linked by equation to the numerical value of physical constant reduced Planck constant. The steps preferably should not be anything different unless every index were rescaled. By way of example, without limitation, using numbers like 1.0545 and 2×1.0545 in place of integer indexes, the steps then are 28.4715 and 75.924 instead of 27 and 72. This or any equivalent method is not considered materially different from the algorithm specified here.

Should calculated values of the index be even, method 600 may progress to even index value operation 614 that may progress method 600 to subtraction operation 620 where 72 may be subtracted from the odd index calculated value at operation 612 prior to culmination of method 600 at end operation 628. Those skilled in the art will appreciate that the exact number values subtracted at subtraction operation 620 may be different than 72, e.g., higher or lower, depending on the calculative metric employed by method 600 without departing from the scope and spirit of the disclosed embodiments.

Index values intended to be calculated on behalf of enzymes 608, e.g., as may be determined by any one or more of the index value calculative methods previously presented and discussed, may be further augmented or numerically manipulated, e.g., for odd index values, at odd index value operation 616 that may progress method 600 addition operation 622 where 27 is added to the calculated index value and index operation 624 where 72 is added to the calculated index value prior to culmination of method 600 at end operation 628. Those skilled in the art will appreciate that the exact number values added at addition operations 622 and 624 may be different than 27 and 72, respectively, e.g., higher or lower, depending on the calculative metric employed by method 600 without departing from the scope and spirit of the disclosed embodiments.

Index values intended to be calculated on behalf of analogs 610, e.g., as may be determined by any one or more of the index value calculative methods previously presented and discussed, may be further augmented or numerically manipulated at index operation 626 that may progress method 600 to end operation 628. Those skilled in the art will appreciate that numerical manipulation at index operation 626 may include any number of transformations without departing from the scope and spirit of the disclosed embodiments.

Figure 7:
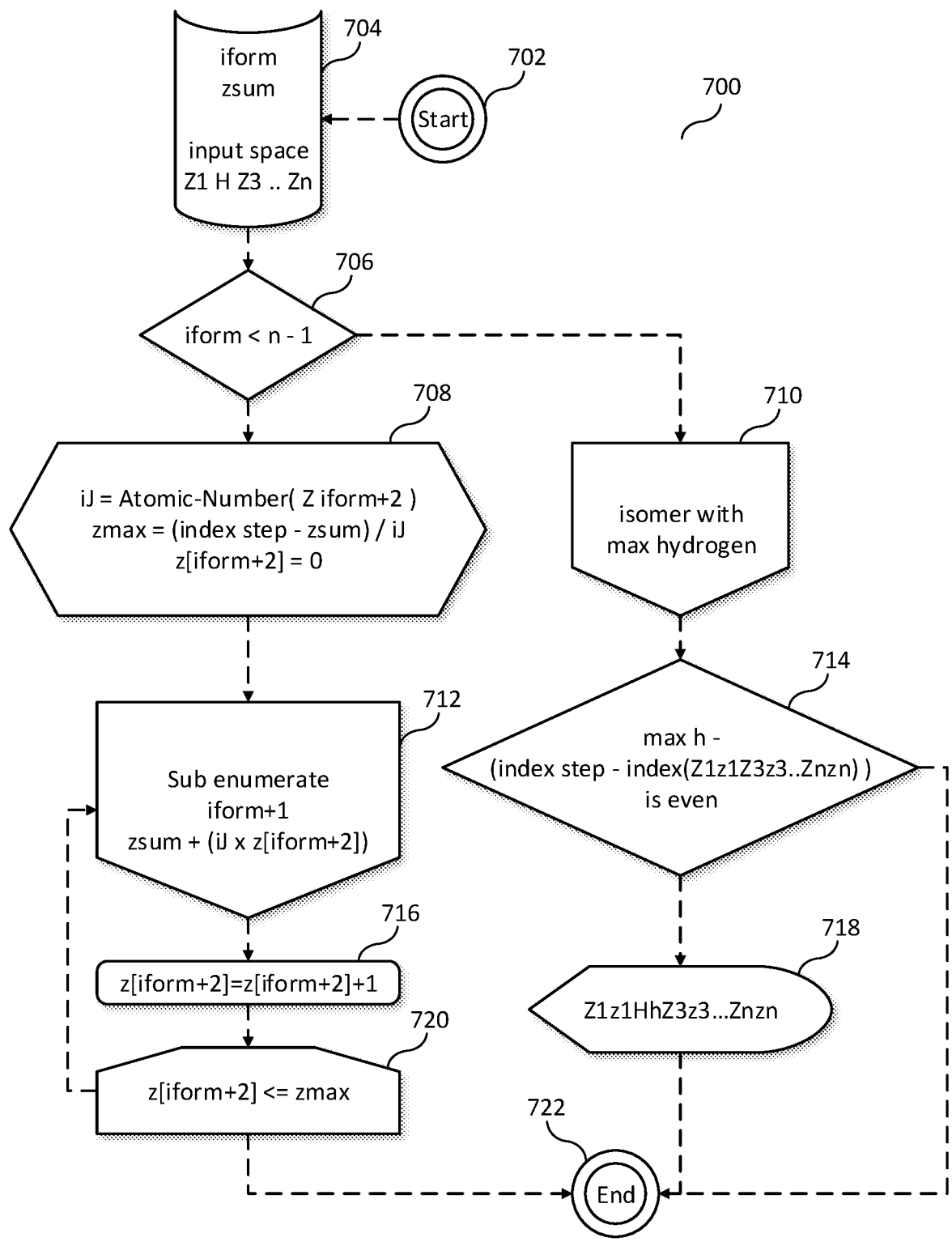
FIG. 7 illustrates a flowchart of an exemplary method of a sub-enumeration calculation operation, in accordance with an embodiment of the present invention.

FIG. 7 illustrates a flowchart of an exemplary method of a sub-enumeration calculation operation, in accordance with an embodiment of the present invention. In the present embodiment, method 700 may be employed to enumerate and/or sub-enumerate at least portions of chemical formulas as may be associated for subsequent search related purposes, e.g., to locate, uncover, and return search results related to that input. Accordingly, method 700 may begin at start operation 702 to progress to operation 704 where iform and zsum operations may involve the input of chemical formulas in the general format of Z1 H Z3 . . . Zn etc., prior to progressing to operation 706 that may assess whether such iform calculations are at least one integer value beneath a set value "n".

Method 700 may then progress to operations 708 and 710. Operation 708 calculates a value for iJ as equal to an atomic number that may be numerically manipulated or transformed, e.g., having 2 added thereto, where other such values including zmax may be calculated as (index step−zsum)/iJ, where further numerical increments and/or adjustments are possible, including assessments, e.g., z[iform+2] =0. Operation 710 may perform calculative operations similar to that described for operation 708 for an isomer with a maximum possible hydrogen count, e.g., permitting for a stable chemical compound, etc., and/or include other or different calculative operations. A guiding aspect of method 700 is to go through the possible values like N0, N1 . . . rejecting all combinations that give the wrong index value, example dichlorobenzine byproduct C2 index step 134 rejects C0H_N0O17 because O-O- . . . -O-O can only have canonical isomer H-O17-H which would give it 17×8+ 2=136 not equal index step 134. Input dichlorobenzine and byproduct C2 in search space C_H_N_O_ the algorithm listed 541 formulas and rejected 969 formulas. Subsequent to operation 708, operation 712 performs a sub enumerate calculation involving iform values considered earlier to increment the same by one integer value, e.g, iform+1, and/or additional numerical manipulations such as zsum+ (iJ×z[iform+2]). Those skilled in the art will appreciate that the example terms "zsum" and "iform" are provided as an example and that other terms may be used for describing and/or referring to numerical values associated with enumeration of chemical formulas without departing from the scope and spirit of the disclosed embodiments.

Method 700 may progress to operation 716 that further numerically manipulates number values according to: z[iform+2]=z[iform+2]+1, and then operation 720, which performs: z[iform+2]<=zmax, to increment enumerated values systematically until a maximum, e.g., zmax, is reached prior to culmination of method 700 at end operation 722.

Subsequent to operation 710, operation 714 performs a max hydrogen ("h") index step to ensure that total number of enumerated hydrogen values are even prior culmination of method 700 at end operation 722. Alternatively, by way of example and not limitation, operation 714 may progress to operation 718 involving representation of chemical formulas incoming or input thereto in the form of Z1z1HhZ3z3 . . . Znzn prior culmination of method 700 at end operation 722.

Figure 8:
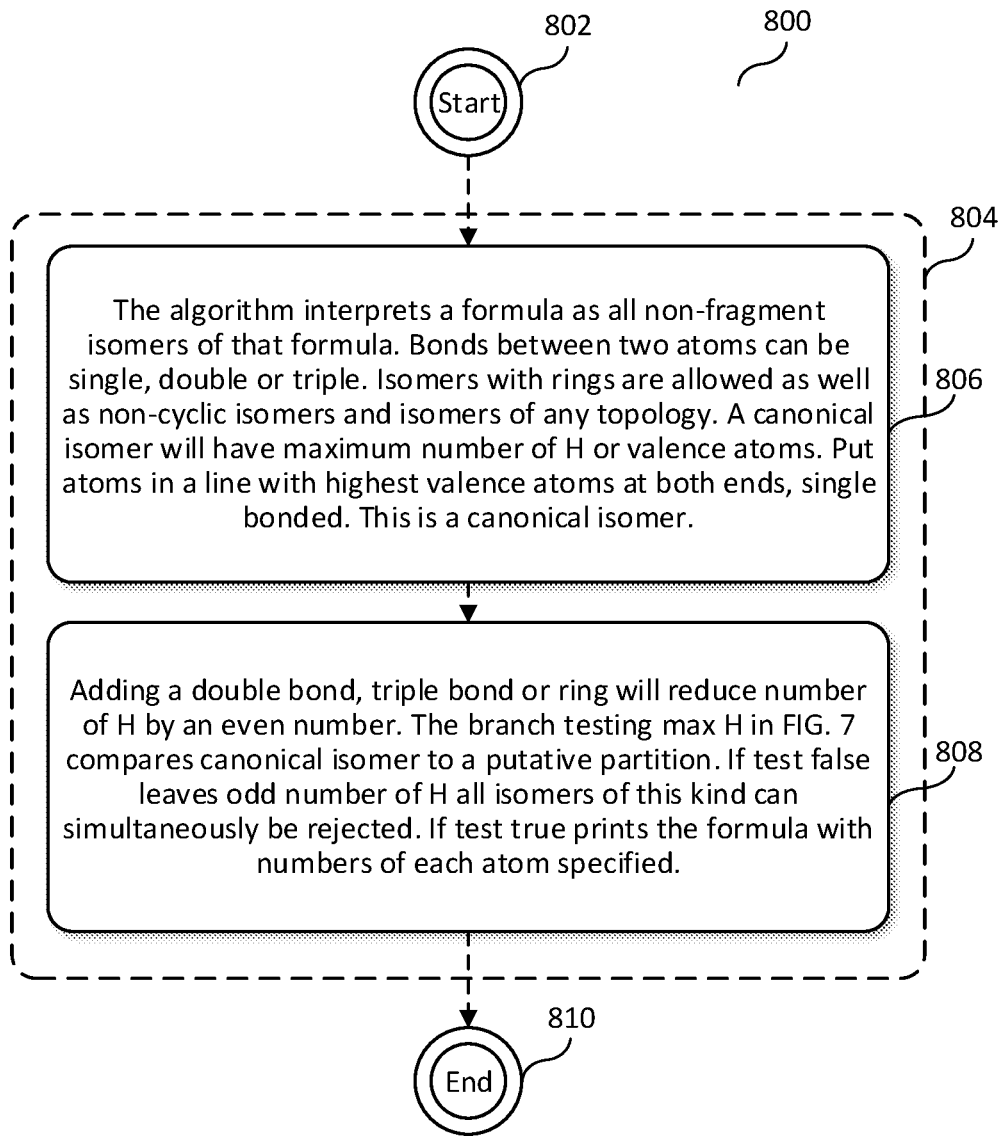
FIG. 8 illustrates a flowchart of an exemplary method of algorithm interpretation regarding bonds between atoms, in accordance with an embodiment of the present invention.

FIG. 8 illustrates a flowchart of an exemplary method of algorithm interpretation regarding bonds between atoms, in accordance with an embodiment of the present invention. In the present embodiment, method 800 may be implemented at least partially in conjunction with any one or more of the methods and/or algorithms presented earlier and may begin at start operation 802. Next, at operation 806, method 800 may involve or otherwise employ an algorithm that interprets any input formula thereto as all non-fragment isomers of that formula and may consider at least the following example conditions: bonds between two atoms can be single, double or triple; isomers with rings may be allowed as well as non-cyclic isomers and isomers of any topology; a canonical isomer may have maximum number of H or valence atoms; atoms may be placed in a line with highest valence atoms at both ends, single bonded, where such a configuration may be referred to as a canonical isomer.

Method 800 may progress to operation 808 after operation 806 where, by way of example and not limitation, any one or more of the following example operations regarding data manipulation or transformation may be performed regarding the enumeration of input chemical formulas: adding a double bond, triple bond or ring will reduce number of H by an even number; the branch testing max H in FIG. 7 compares canonical isomer to a putative partition; if test "false" leaves an odd number of H—all isomers of this kind can simultaneously be rejected; if test "true" prints a formula with numbers of each atom specified, prior to culmination of method 800 at end operation 810. Operations 806 and 808 may be collectively referred to as group operation 804. Those skilled in the art will appreciate that additional or fewer transformation may be applied to algorithms associated with the enumeration of chemical formulas as disclosed herein without departing from the scope and spirit of the disclosed embodiments.

Figure 9:
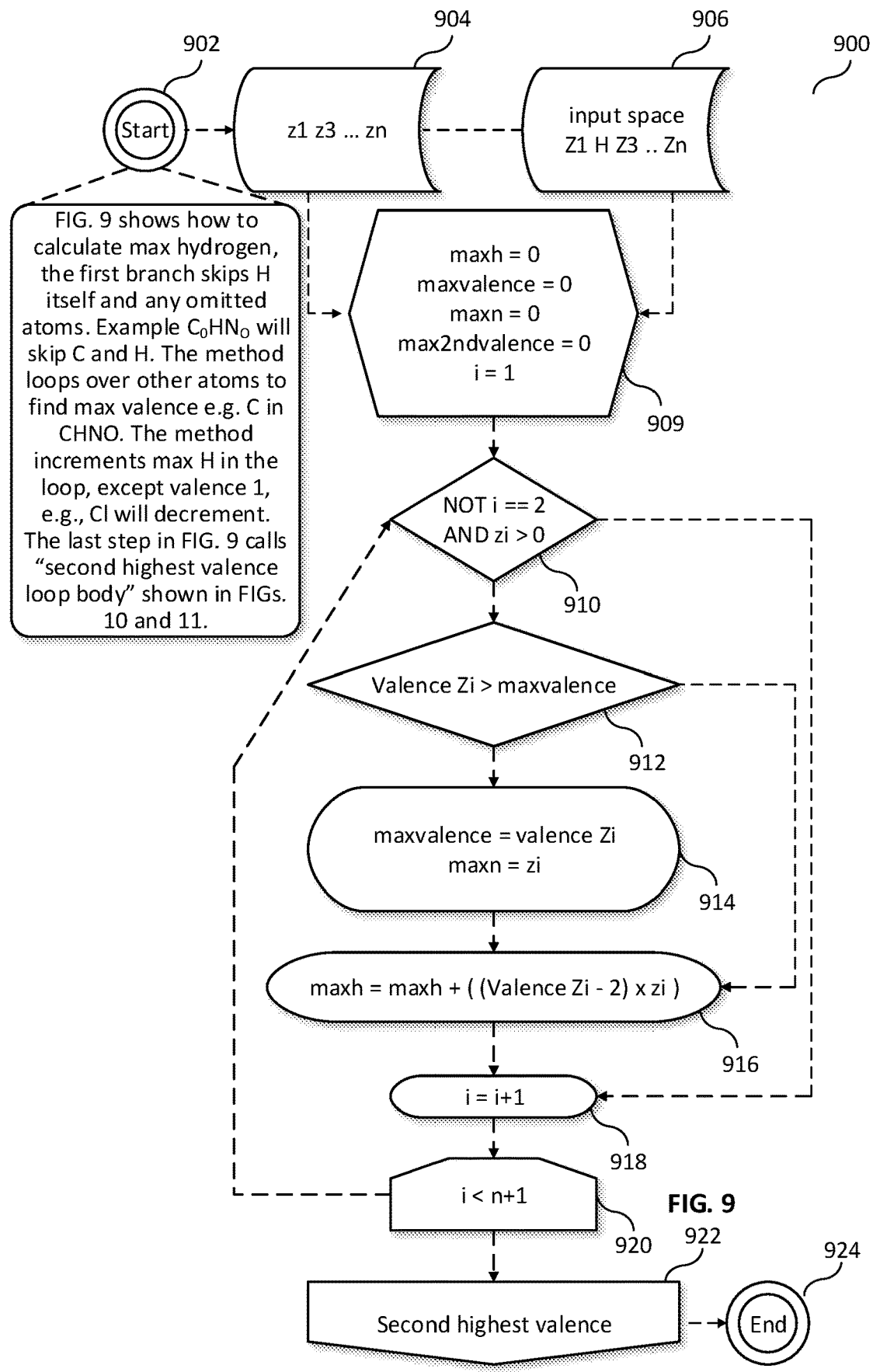
FIG. 9 illustrates a flowchart of an exemplary method of calculating and/or identifying an isomer with a maximum number of hydrogen atoms, in accordance with an embodiment of the present invention.

FIG. 9 illustrates a flowchart of an exemplary method of calculating and/or identifying an isomer with a maximum number of hydrogen atoms, in accordance with an embodiment of the present invention. In the present embodiment, method 900 shown in FIG. 9 shows how to calculate max hydrogen, the first branch skips H itself and any omitted atoms. By way of example and not limitation, in one or more embodiments, $C_0HN_O$ will skip C and H. The method loops over other atoms to find max valence e.g. C in CHNO. The method increments max H in the loop, except valence 1, e.g., C1 will decrement. The last step in method 900 calls "second highest valence loop body" shown in FIGS. 10 and 11. Enzymes for NH2 with search space C_H_ is a simple example with C0, C1, C2, C3, C4 rejected but C5H6 the only answer. Method 909 initialises variables. For C0 method 910 i=1 z1=0 false, proceeds to method 918 i=2 loops back to 910 false then method 918 i=3 then method 920 tests false exiting to method 922 Second highest valence. For C1 method 910 i=1 z1=1 tests true, then method 912 valence C=4>0 tests true, then method 914 maxvalence=4 maxn=1, method 916 maxh incremented (4−2)×1=2, method 918 i=2, then method 920 loops back to method 910. Method 910 tests false to skip Hydrogen then method 918 i=3 then method 920 tests false exiting to method 922 Second highest valence. For C2 method 910 i=1 z1=2 tests true, then method 912 valence C=4>0 tests true, then method 914 maxvalence=4 maxn=2, method 916 maxh incremented (4−2)×2=4, then method 918 i=2, then method 920 loops back to method 910. Method 910 tests false to skip Hydrogen then method 918 i=3 then method 920 tests false exiting to method 922 Second highest valence. C3 to C5 are similar with z1 ranging 3 to 5 and maxn ranging 3 to 5 and maxh incremented 6 to 10 in method 910, further incremented 2 in method 1010. C0 to C4 don't have enough electrons to reach the required number 9+27=36 but C5H6 has exactly the right number.

It should be noted that the use of computer system in most practical applications requires careful considerations by those the skilled in the art at least because among 40 isomers of C5H6 is a ring shaped toxic molecule. Prior art software like MOLGEN or OMG may be used on C5H6 to find isomers. Gugisch, R., Kerber, A., Kohnert, A., Laue, R., Meringer, M., Rücker, C., Wassermann, A.: MOLGEN 5.0, A Molecular Structure Generator (2016) Advances in Mathematical Chemistry and Applications: Revised Edition, 1, pp. 113-138. Peironcely, J. E., Rojas-Chertó, M., Fichera, D., Reijmers, T., Coulier, L., Faulon, J. L., & Hankemeier, T. (2012). OMG: Open Molecule Generator. *Journal of cheminformatics*, 4(1), 21. doi:10.1186/1758-2946-4-21 https://www.ncbi.nlm.nih.gov/pmc/articles/PMC3558358/

Method 900 may begin at start operation 902 from which increment operation 904 may assess chemical formula values through "zn" where subsequently a user of method 900 may optionally input a chemical space intended to be searched at input space operation 906 prior to progressing to max h assessment operation 909 where a maximum number of hydrogen and/or valences may be tabulated, calculated, identified and/or otherwise assessed. Next, method 900 may progress to operation 910 where incremental values of calculated indexes, e.g., "i", may be assessed to determine position for subsequent method progression. That is, should assessed index values "i" be not equal to a specified value, e.g., 2, and another pre-set condition be satisfied, e.g., and incremental values of assessments of index values for various parts of a given chemical formula, etc., then method 900 may either progress to a maximum valence assessment operation 912 or bypass said operation, and other operations 912-916, to forward to increment operation 918 to count and calculate additional i values for isomer possibilities to identify an isomer for a given input chemical formula with a maximum H value.

Alternative to the bypass as described above, various data transformation operations 912-916 may systematically assess maximum hydrogen values for related isomers in input chemical space, e.g., as done so at operation 906, by considering (at a minimum) valence hydrogen and/or isomer configurations, where index values less than a specified value may be returned at operation 920 to operation 910 or forwarded to a second highest valence hydrogen assessment operation 922 prior to culmination of method 900 at end operation 924.

Figure 10:
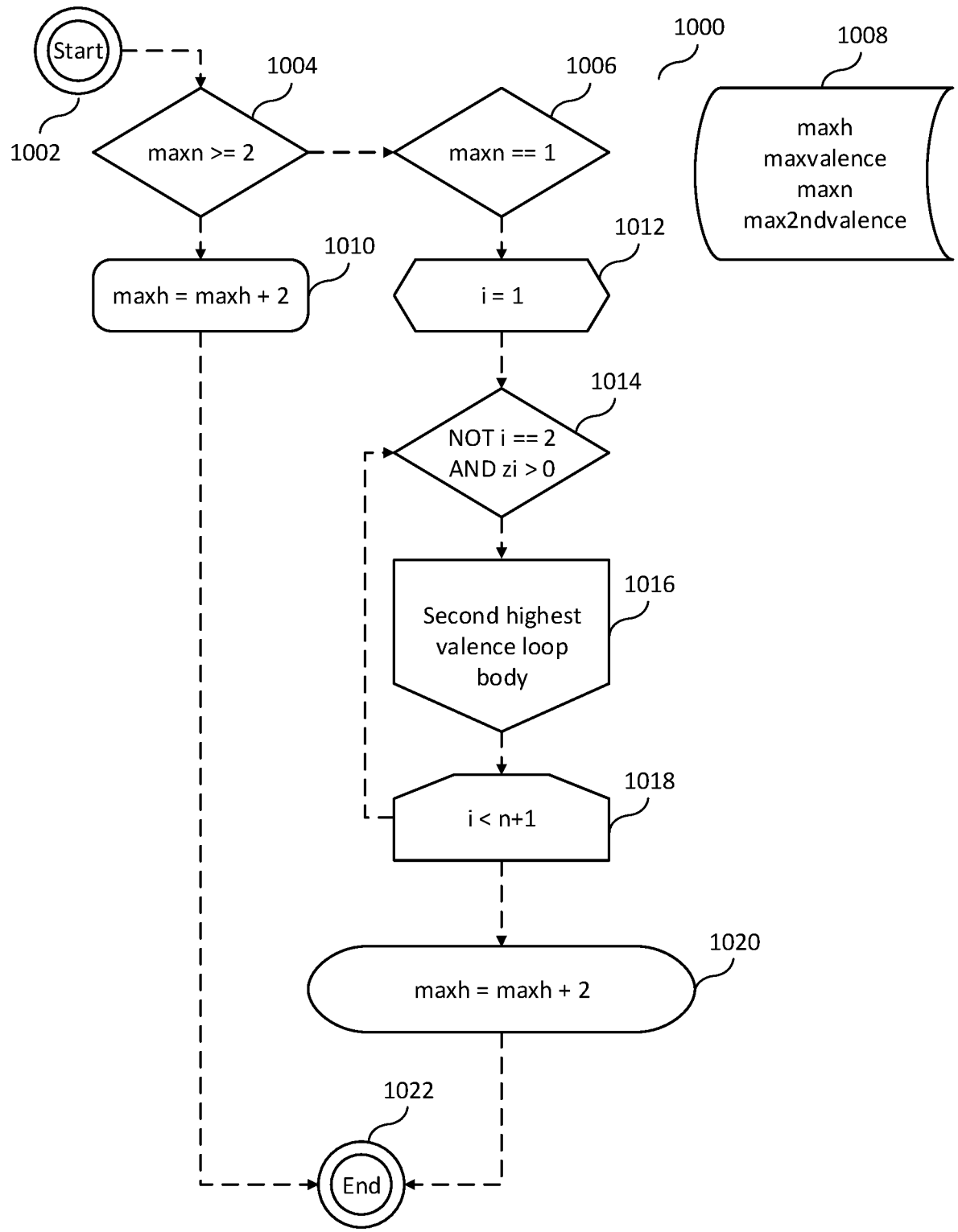
FIG. 10 illustrates a flowchart of an exemplary method of calculating and/or identifying an isomer with a second-highest number of valencies, in accordance with an embodiment of the present invention.

FIG. 10 illustrates a flowchart of an exemplary method of calculating and/or identifying an isomer with a second-highest number of valencies, in accordance with an embodiment of the present invention. In the present embodiment, method 1000 may be an embodiment of second highest valence hydrogen assessment operation 922 of method 900 shown in FIG. 9. Method 1000 may begin at start operation 1002 from which it may progress to operation 1004 for assessment of a maximum number of available valencies, e.g., that must be greater than or equal to 2, prior to progression of various additional operations. Should a maxh (e.g., a maximum hydrogen) value be assessed in increments of 2 at operation 1010, then method 1000 may progress directly to end operation 1022 to culminate therein.

Alternatively, other calculative procedures exist whereby method 1000 progresses to assessment of a max index or increment value, e.g., beginning from 1. Those skilled in the art will appreciate that repository 1008 may include various types of stored information concerning maximum identified hydrogens, valencies, atomic numbers, and/or second valencies and such considerations may be at least partially assessed by method 1000 throughout.

Subsequent to operation 1006, operations 1012-1020 may, at least partially according to the mathematical formulas depicted therein, incrementally parse through input chemical formulas to determine second-highest available vacancy positions prior to culmination of method 1000 at end operation 1022.

Figure 11:
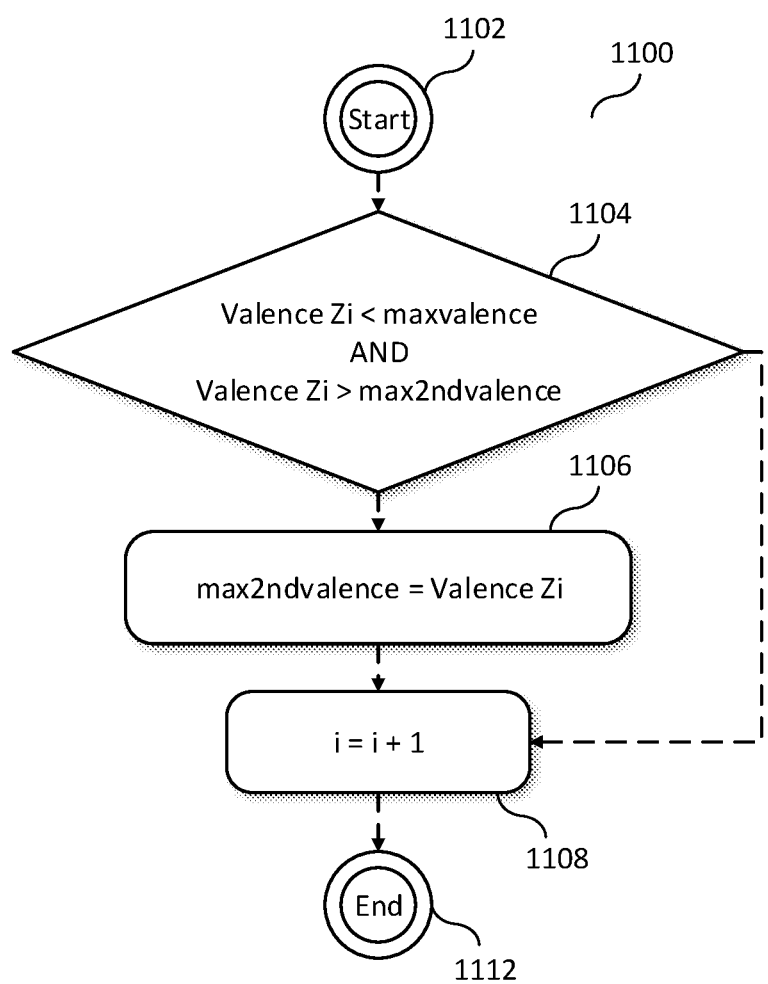
FIG. 11 illustrates a flowchart of an exemplary method of that included in the "second highest valence loop body" shown in FIG. 10, in accordance with an embodiment of the present invention.

FIG. 11 illustrates a flowchart of an exemplary method of that included in the "second highest valence loop body" shown in FIG. 10, in accordance with an embodiment of the present invention. In the present embodiment, operation 1016 of method 1000 shown in FIG. 10 is shown in more detail. By way of example and not limitation, in one or more embodiments, method 1100 may begin at start operation 1102 from which valencies may be calculated according to at least partial satisfaction of the mathematical conditions set forth by operation 1104, that is: Valence $Z_i$<maxvalence AND Valence $Z_i$>max2ndvalence, e.g., where such a successful assessment of such conditions may result in the identification of a second highest valency count for a given input chemical formula resulting in appropriate identification and/or enumeration thereof at operation 1106 prior to incrementing forward at operation 1108 and culmination at end operation 1112.

Figure 12:
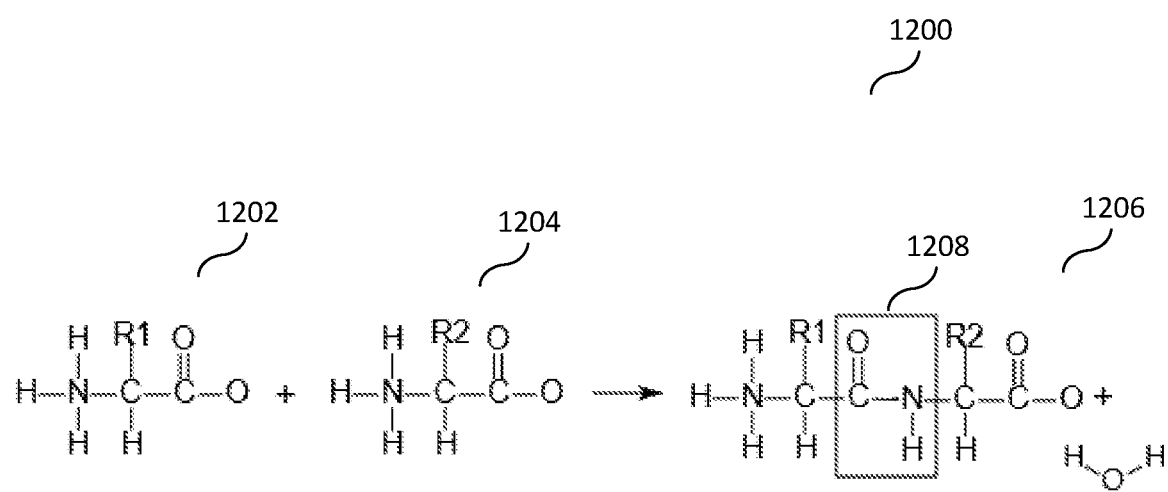
FIG. 12 illustrates an example chemical reaction, in accordance with an embodiment of the present invention.

FIG. 12 illustrates an example chemical reaction, in accordance with an embodiment of the present invention. In the present embodiment, reaction 1200 may include a first and second reagent 1202, 1204, respectively, which yields product 1206 featuring CHNO group 1208 contained therein, where any one or more of the algorithms and/or methods discussed herein may be used to analyze, process, consider and/or assess any one or more of the chemical formulas, species, moieties, structures, reagents, products and/or the like of that shown in reaction 1200. An index of 22 may be ascribed to the CHNO group 1208 on account of tabulation via traditional means of an index number being equivalent to the atomic number of the constituent atoms of a given chemical group, etc.

Figure 13A:
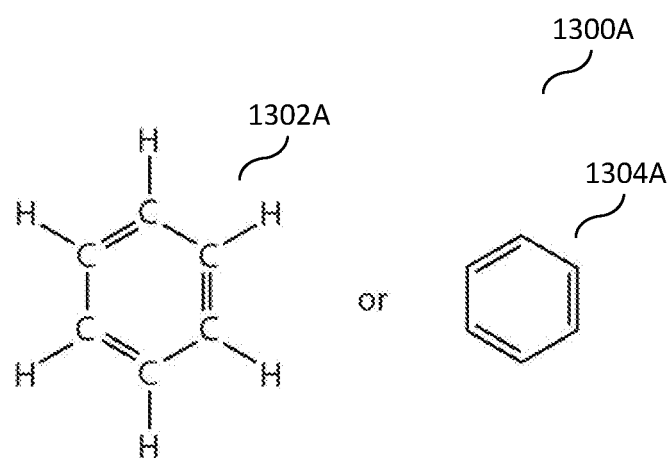
FIG. 13A-B illustrate an example structure of benzene, in accordance with an embodiment of the present invention.
Figure 13B:
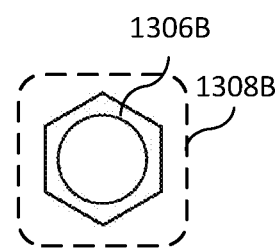

FIG. 13A-B illustrate an example structure of benzene, in accordance with an embodiment of the present invention. In the present embodiment, benzene is understood to be an organic chemical compound with the chemical formula $C_6H_6$. The benzene molecule is composed of six carbon atoms joined in a ring with one hydrogen atom attached to each. As it contains only carbon and hydrogen atoms, benzene is classed as a hydrocarbon.

Various depictions of benzene are shown for illustrative purposes including depiction 1300A and 1308A. Depiction 1300A includes chemical structures 1302A and 1304A showing various double bonds between constituent carbon atoms, where depiction 1308B more clearly emphasizes the uniform resonance structure 1306B of benzene. Any one or more of the algorithms discussed herein may calculate and/or otherwise tabulate appropriate index values for example chemical structures such as benzene within various defined or un-defined chemical spaces. Those skilled in the art will appreciate that shown as benzene is provided as an example only and that various other chemical structures may alternatively be searched for without departing from the scope and spirit of the disclosed embodiments.

FIG. 14 illustrates a table of search results to target benzene, in accordance with an embodiment of the present invention. In the present embodiment, input of benzene for enumeration and searching of a defined chemical space as may be associated with any one or more of the algorithms and/or methods presented herein may result in any one or more of the shown chemical structures and/or formulas, including: Spermine, Indanidine, Quipazine, Atipamezole, Napamezole, β-bisabolene, β-cadinene, Δ-capnellene. Such computations involve too many steps to list here even though a computer performs them in seconds.

Figure 15:
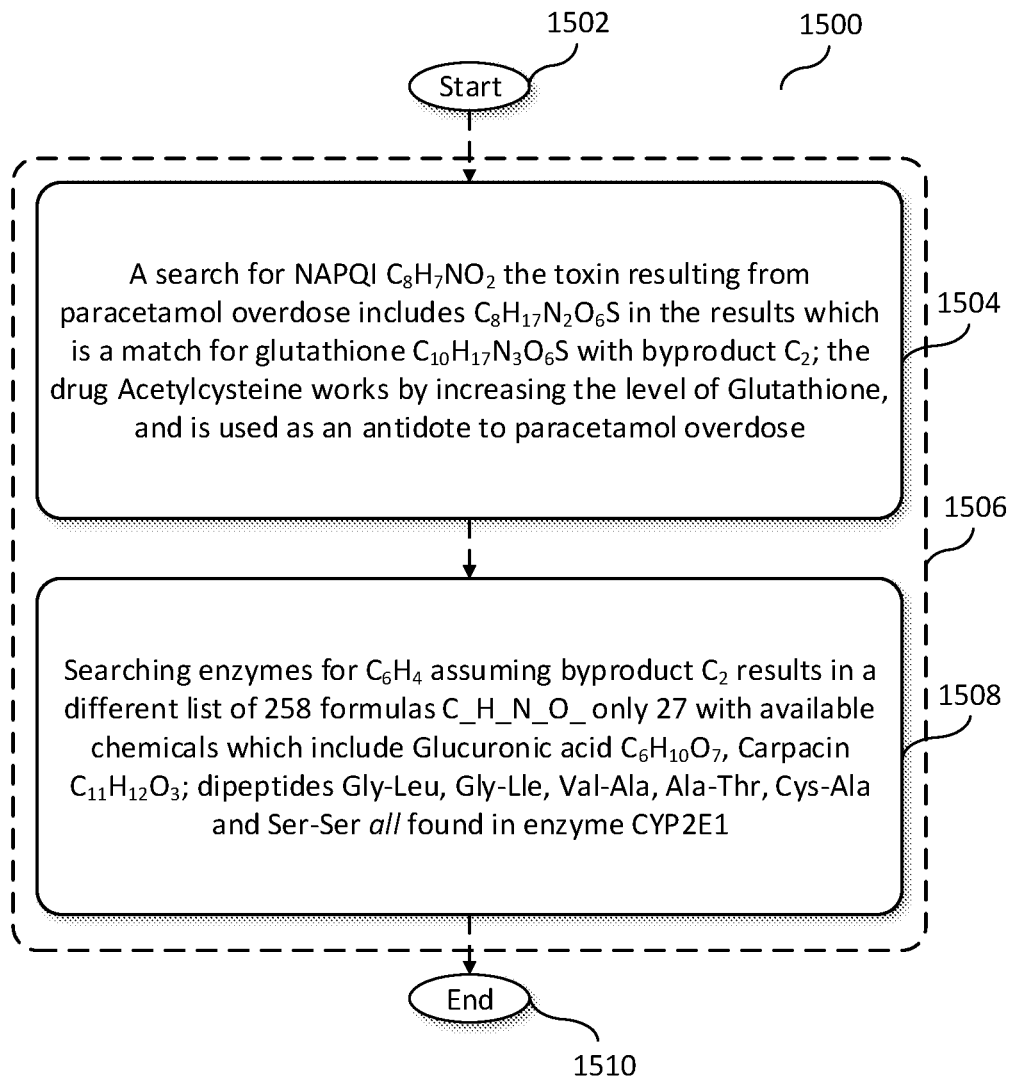
FIG. 15 illustrates a flowchart of an exemplary method of a search for NAPBQI, a toxic byproduct produced during the xenobiotic metabolism of the analgesic paracetamol, in accordance with an embodiment of the present invention.

FIG. 15 illustrates a flowchart of an exemplary method of a search for NAPQI, a toxic byproduct produced during the xenobiotic metabolism of the analgesic paracetamol, in accordance with an embodiment of the present invention. In the present embodiment, method 1500 may be conducted by any one or more of the algorithms and/or methods shown and discussed herein. Method 1500 may begin with start operation 1502 from which operation 1504 may perform at least: a search for NAPQI $C_8H_7NO_2$ the toxin resulting from paracetamol overdose that includes $C_8H_{17}N_2O_6S$ in the results which is a match for glutathione $C_{10}H_{17}N_3O_6S$ with byproduct $C_2$; the drug Acetylcysteine works by increasing the level of Glutathione, and is used as an antidote to paracetamol overdose. Next, operation 1508 may perform at least: searching enzymes for $C_6H_4$ assuming byproduct $C_2$ results in a different list of 258 formulas C_H_N_O_ only 27 with available chemicals which include Glucuronic acid $C_6H_{10}O_7$, Carpacin $C_{11}H_{12}O_3$; dipeptides Gly-Leu, Gly-Lle, Val-Ala, Ala-Thr, Cys-Ala and Ser-Ser all found in enzyme CYP2E1. Operations 1504 and 1508 may collectively be referred to as group operation 1506. Method 1500 may then culminate at end operation 1510. Those skilled in the art will appreciate that various modifications may be made to operations 1504 and 1508 without departing from the scope and spirit of the disclosed embodiments.

FIG. 16 illustrates a table of enzyme displayed in codified format, in accordance with an embodiment of the present invention. In the present embodiment, table 1600 may be considered by any one or more of the calculative procedures, algorithms, processes and/or methods discussed herein while searching chemical space for related chemical formulas, structures and/or the like relative to an input chemical formula. Those skilled in the art will appreciate that deviations may be made from that displayed in table 1600 without departing from the scope and spirit of the presently disclosed embodiments. For instance, various segments of the codified enzymes may be identified and considered for search-related organizational purposes.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied. Such computers referenced and/or described in this disclosure may be any kind of computer, either general purpose, or some specific purpose computer such as, but not limited to, a workstation, a mainframe, GPU, ASIC, etc. The programs may be written in C, or Java, Brew or any other suitable programming language. The programs may be resident on a storage medium, e.g., magnetic or optical, e.g., without limitation, the computer hard drive, a removable disk or media such as, without limitation, a memory stick or SD media, or other removable medium. The programs may also be run over a network, for example, with a server or other machine sending signals to the local machine, which allows the local machine to carry out the operations described herein.

Design Variations

Those skilled in the art will appreciate that any one or more of the algorithms, calculative procedures, values, identifications, data transformations, enumeration schemes and/or numerical assignments may be varied without limitation. For example, such variants may include at least: a variant of the input can accept an isomer in any representation such as InCh1 or parse a formula from text; a variant of the algorithm is given a reaction byproduct and searches against the remainder of the molecule; a common byproduct in antidotes and enzymes may be $C_2$; deduction of an index of a byproduct from index of an input molecule; another variant of the algorithm finds protein sequences instead of general molecules; input may be to enumerate a list of indexes of each alpha amino acid instead of atomic numbers; valences may be set to always two; the free dipeptide Proline-Proline may be uniquely identified for Benzine; the enzyme CYP2E1 may be effectively fingerprinted by seven dipeptides identified for Benzine with byproduct C2; another variant of the algorithm may be to find drug resistance candidates, and to find drugs or protein sequences specifically targeting the drug resistance candidates.

Additional variants include: using a random isomer or more than one isomer in place of the canonical isomer; using coordinate representation or bracket representation or s p d f or other schemes in place of the canonical isomer; using a fictitious atom or radioactive atom to get around oxidation number or stability restrictions; using an equivalent index representation by multiplying or dividing by a factor; and. to repeat the algorithm over a database and or filter the output whether useful or not.

Another variant of the algorithm is to enumerate isomers and then compare the shape of the target molecule with the shape of each prospective isomer. The Euclidean shape spaces are particularly suited because there is a Le Bhavnagri distance formula [source: H. Le and B. Bhavnagri, On simplifying shapes by subjecting them to collinearity constraints, Mathematical Proceedings of the Cambridge Philosophical Society, Volume 122 no 2, September 1997, pp 315-323] for comparing shapes with different numbers of points. Pairwise consistency is weakly defined in terms of superimposition of Euclidean similarities always being one to one [source: B. Bhavnagri, An index of carcenogenesis using pairwise consistency, MODSIM 2013]; inconsistency means there is a pair of superimposed Euclidean similarities which are not one to one.

Yet another variant of the algorithm is to enumerate isomers and then compare the size and shape of the target molecule with the shape of each prospective isomer. This is different from the above variant in that size information is retained.

Integration with Client/Server System

Figure 17:
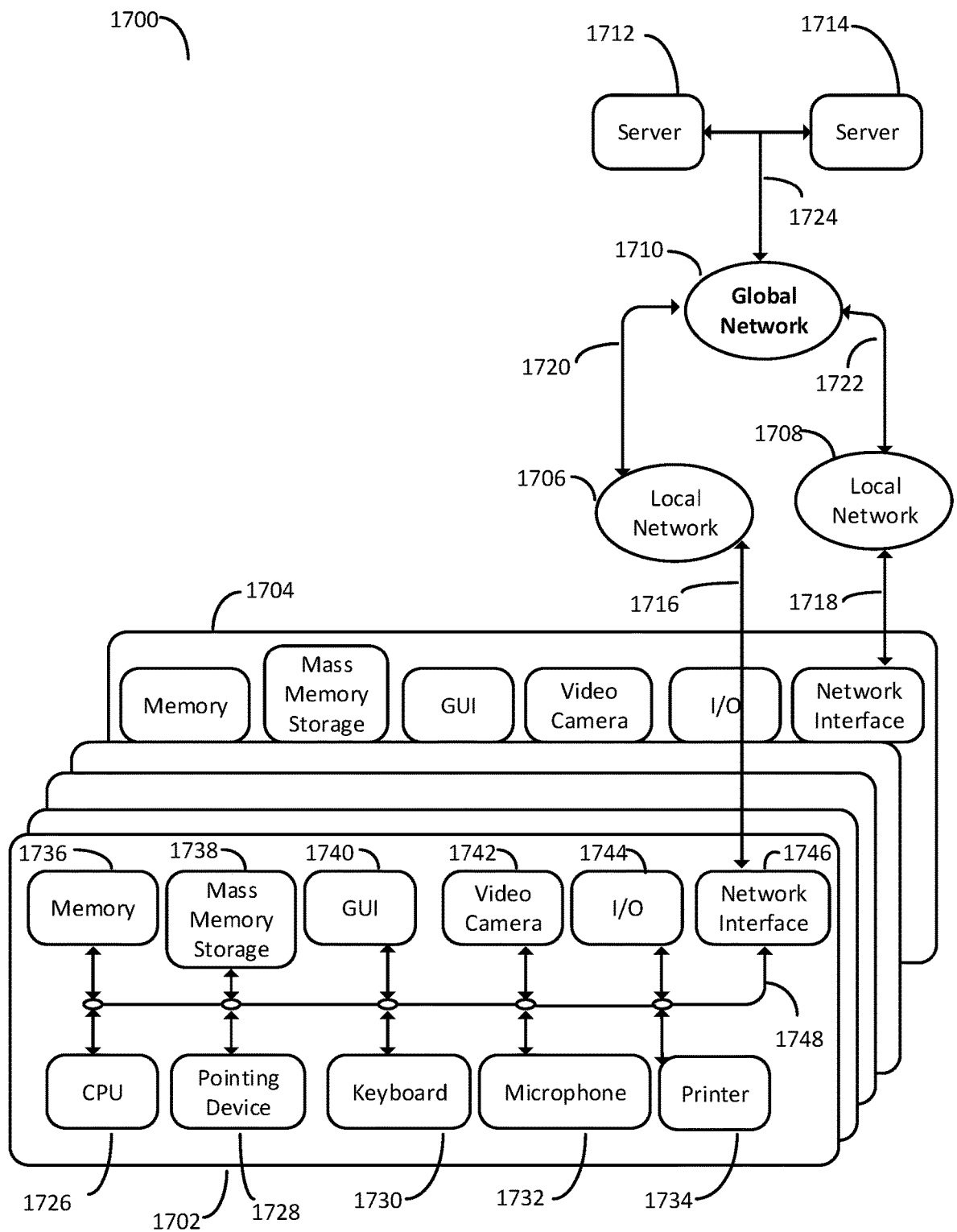
FIG. 17 illustrates a block diagram depicting an exemplary client/server system which may be used by an exemplary web-enabled/networked embodiment of the present invention.

FIG. 17 is a block diagram depicting an exemplary client/server system which may be used by an exemplary web-enabled/networked embodiment of the present invention.

A communication system 1700 includes a multiplicity of clients with a sampling of clients denoted as a client 1702 and a client 1704, a multiplicity of local networks with a sampling of networks denoted as a local network 1706 and a local network 1708, a global network 1710 and a multiplicity of servers with a sampling of servers denoted as a server 1712 and a server 1714.

Client 1702 may communicate bi-directionally with local network 1706 via a communication channel 1716. Client 1704 may communicate bi-directionally with local network 1708 via a communication channel 1718. Local network 1706 may communicate bi-directionally with global network 1710 via a communication channel 1720. Local network 1708 may communicate bi-directionally with global network 1710 via a communication channel 1722. Global network 1710 may communicate bi-directionally with server 1712 and server 1714 via a communication channel 1724. Server 1712 and server 1714 may communicate bi-directionally with each other via communication channel 1724. Furthermore, clients 1702, 1704, local networks 1706, 1708, global network 1710 and servers 1712, 1714 may each communicate bi-directionally with each other.

In one embodiment, global network 1710 may operate as the Internet. It will be understood by those skilled in the art that communication system 1700 may take many different forms. Non-limiting examples of forms for communication system 1700 include local area networks (LANs), wide area networks (WANs), wired telephone networks, wireless networks, or any other network supporting data communication between respective entities.

Clients 1702 and 1704 may take many different forms. Non-limiting examples of clients 1702 and 1704 include personal computers, personal digital assistants (PDAs), cellular phones and smartphones.

Client 1702 includes a CPU 1726, a pointing device 1728, a keyboard 1730, a microphone 1732, a printer 1734, a memory 1736, a mass memory storage 1738, a GUI 1740, a video camera 1742, an input/output interface 1744 and a network interface 1746.

CPU 1726, pointing device 1728, keyboard 1730, microphone 1732, printer 1734, memory 1736, mass memory storage 1738, GUI 1740, video camera 1742, input/output interface 1744 and network interface 1746 may communicate in a unidirectional manner or a bi-directional manner with each other via a communication channel 1748. Communication channel 1748 may be configured as a single communication channel or a multiplicity of communication channels.

CPU 1726 may be comprised of a single processor or multiple processors. CPU 1726 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors.

As is well known in the art, memory 1736 is used typically to transfer data and instructions to CPU 1726 in a bi-directional manner. Memory 1736, as discussed previously, may include any suitable computer-readable media, intended for data storage, such as those described above excluding any wired or wireless transmissions unless specifically noted. Mass memory storage 1738 may also be coupled bi-directionally to CPU 1726 and provides additional data storage capacity and may include any of the computer-readable media described above. Mass memory storage 1738 may be used to store programs, data and the like and is typically a secondary storage medium such as a hard disk. It will be appreciated that the information retained within mass memory storage 1738, may, in appropriate cases, be incorporated in standard fashion as part of memory 1736 as virtual memory.

CPU 1726 may be coupled to GUI 1740. GUI 1740 enables a user to view the operation of computer operating system and software. CPU 1726 may be coupled to pointing device 1728. Non-limiting examples of pointing device 1728 include computer mouse, trackball and touchpad. Pointing device 1728 enables a user with the capability to maneuver a computer cursor about the viewing area of GUI 1740 and select areas or features in the viewing area of GUI 1740. CPU 1726 may be coupled to keyboard 1730. Keyboard 1730 enables a user with the capability to input alphanumeric textual information to CPU 1726. CPU 1726 may be coupled to microphone 1732. Microphone 1732 enables audio produced by a user to be recorded, processed and communicated by CPU 1726. CPU 1726 may be connected to printer 1734. Printer 1734 enables a user with the capability to print information to a sheet of paper. CPU 1726 may be connected to video camera 1742. Video camera 1742 enables video produced or captured by user to be recorded, processed and communicated by CPU 1726.

CPU 1726 may also be coupled to input/output interface 1744 that connects to one or more input/output devices such as such as CD-ROM, video monitors, track balls, mice, keyboards, microphones, touch-sensitive displays, transducer card readers, magnetic or paper tape readers, tablets, styluses, voice or handwriting recognizers, or other well-known input devices such as, of course, other computers.

Finally, CPU 1726 optionally may be coupled to network interface 1746 which enables communication with an external device such as a database or a computer or telecommunications or internet network using an external connection shown generally as communication channel 1716, which may be implemented as a hardwired or wireless communications link using suitable conventional technologies. With such a connection, CPU 1726 might receive information from the network, or might output information to a network in the course of performing the method steps described in the teachings of the present invention.

Figure 18:
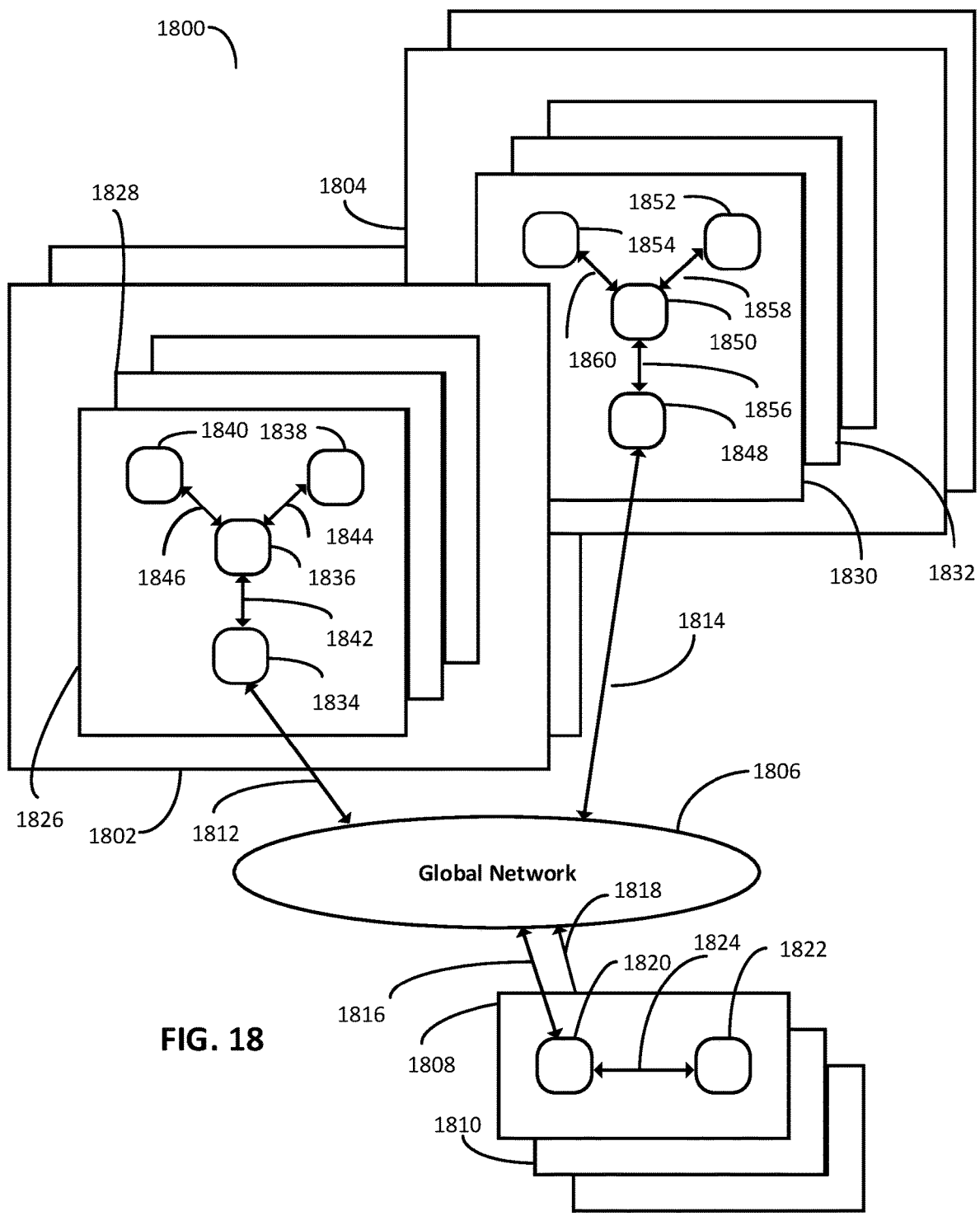
FIG. 18 illustrates a block diagram depicting a conventional client/server communication system, which may be used by an exemplary web-enabled/networked embodiment of the present invention.

FIG. 18 illustrates a block diagram depicting a conventional client/server communication system, which may be used by an exemplary web-enabled/networked embodiment of the present invention.

A communication system 1800 includes a multiplicity of networked regions with a sampling of regions denoted as a network region 1802 and a network region 1804, a global network 1806 and a multiplicity of servers with a sampling of servers denoted as a server device 1808 and a server device 1810.

Network region 1802 and network region 1804 may operate to represent a network contained within a geographical area or region. Non-limiting examples of representations for the geographical areas for the networked regions may include postal zip codes, telephone area codes, states, counties, cities and countries. Elements within network region 1802 and 1804 may operate to communicate with external elements within other networked regions or within elements contained within the same network region.

In some implementations, global network 1806 may operate as the Internet. It will be understood by those skilled in the art that communication system 1800 may take many different forms. Non-limiting examples of forms for communication system 1800 include local area networks (LANs), wide area networks (WANs), wired telephone networks, cellular telephone networks or any other network supporting data communication between respective entities via hardwired or wireless communication networks. Global network 1806 may operate to transfer information between the various networked elements.

Server device 1808 and server device 1810 may operate to execute software instructions, store information, support database operations and communicate with other networked elements. Non-limiting examples of software and scripting languages which may be executed on server device 1808 and server device 1810 include C, C++, C# and Java.

Network region 1802 may operate to communicate bi-directionally with global network 1806 via a communication channel 1812. Network region 1804 may operate to communicate bi-directionally with global network 1806 via a communication channel 1814. Server device 1808 may operate to communicate bi-directionally with global network 1806 via a communication channel 1816. Server device 1810 may operate to communicate bi-directionally with global network 1806 via a communication channel 1818. Network region 1802 and 1804, global network 1806 and server devices 1808 and 1810 may operate to communicate with each other and with every other networked device located within communication system 1800.

Server device 1808 includes a networking device 1820 and a server 1822. Networking device 1820 may operate to communicate bi-directionally with global network 1806 via communication channel 1816 and with server 1822 via a communication channel 1824. Server 1822 may operate to execute software instructions and store information.

Network region 1802 includes a multiplicity of clients with a sampling denoted as a client 1826 and a client 1828. Client 1826 includes a networking device 1834, a processor 1836, a GUI 1838 and an interface device 1840. Non-limiting examples of devices for GUI 1838 include monitors, televisions, cellular telephones, smartphones and PDAs (Personal Digital Assistants). Non-limiting examples of interface device 1840 include pointing device, mouse, trackball, scanner and printer. Networking device 1834 may communicate bi-directionally with global network 1806 via communication channel 1812 and with processor 1836 via a communication channel 1842. GUI 1838 may receive information from processor 1836 via a communication channel 1844 for presentation to a user for viewing. Interface device 1840 may operate to send control information to processor 1836 and to receive information from processor 1836 via a communication channel 1846. Network region 1804 includes a multiplicity of clients with a sampling denoted as a client 1830 and a client 1832. Client 1830 includes a networking device 1848, a processor 1850, a GUI 1852 and an interface device 1854. Non-limiting examples of devices for GUI 1838 include monitors, televisions, cellular telephones, smartphones and PDAs (Personal Digital Assistants). Non-limiting examples of interface device 1840 include pointing devices, mousse, trackballs, scanners and printers. Networking device 1848 may communicate bi-directionally with global network 1806 via communication channel 1814 and with processor 1850 via a communication channel 1856. GUI 1852 may receive information from processor 1850 via a communication channel 1858 for presentation to a user for viewing. Interface device 1854 may operate to send control information to processor 1850 and to receive information from processor 1850 via a communication channel 1860.

For example, consider the case where a user interfacing with client 1826 may want to execute a networked application. A user may enter the IP (Internet Protocol) address for the networked application using interface device 1840. The IP address information may be communicated to processor 1836 via communication channel 1846. Processor 1836 may then communicate the IP address information to networking device 1834 via communication channel 1842. Networking device 1834 may then communicate the IP address information to global network 1806 via communication channel 1812. Global network 1806 may then communicate the IP address information to networking device 1820 of server device 1808 via communication channel 1816. Networking device 1820 may then communicate the IP address information to server 1822 via communication channel 1824. Server 1822 may receive the IP address information and after processing the IP address information may communicate return information to networking device 1820 via communication channel 1824. Networking device 1820 may communicate the return information to global network 1806 via communication channel 1816. Global network 1806 may communicate the return information to networking device 1834 via communication channel 1812. Networking device 1834 may communicate the return information to processor 1836 via communication channel 1842. Processor 18186 may communicate the return information to GUI 18188 via communication channel 1844. User may then view the return information on GUI 1838.

Advantages

The presently disclosed embodiments provide algorithmic methods, executed at least partially by processors of a computer, allowing for the convenient navigation of vast chemical space based on the input of one or more identifying pieces of information, including chemical structures and/or the like. Iterations of the algorithms may be created in the form of computer software distributable with a commercial license, or be otherwise be made in trial and/or full versions on a free basis as freeware.

Moreover, iterations of the presently disclosed embodiments may at least consider or account for accepting input information and/or conditions regarding at least the following as commonly encountered in the field of, for example (but not limitation thereto): industrial chemistry, which can consider temperature, pressure, radiation and other energy barrier breaking methods e used together with synthetic catalysts. Further, information concerning enzymes may also be input, where such enzymes may function under very mild conditions of temperature and pH without necessarily requiring physical condition manipulations. Enzymes may also be highly specific for their substrates, where the disclosed, methods may accommodate the convenient searching thereof.

Providing for robust computational and combinatorial techniques, the disclosed embodiments efficiently navigate the sheer vast size of chemical space, considering and/or reviewing huge numbers of natural and synthetic molecules, a diversity of carcinogens, and consider apparent lacks of anisotropy and so on and so forth.

Disclosed embodiments further also consider enumerations and the numerical reduction thereof to identified integer values such as 0, 1, and 2 to, for example (but not limitation thereto) evaluate consistency, as well as employing multiple nested loops to consider certain and/or all periods of the periodic table, etc.

Numerical patterns were also observed across a variety of chemical reactions to set offset and/or calculative measures, such as a step of 27, which may be of particular value for certain atoms and lower index alpha amino acids, but not others.

Trial-and-error computational training approaches applied to chemical formula fragments employing previous methods produced incorrect structures concerning searching carcinogens, thus application of 72 as an offset calculative numerical figure was derived to produce usable and quality solutions.

Considerations of representational consistency as developed earlier may find applications as disclosed herein to better characterize chemical compounds suitable for the treatment of ailments such as cancer such as that phosphorous usually reverses inconsistency and so on and so forth.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention. Thus, some alternate embodiments of the present invention may be configured to comprise a smaller subset of the foregoing means for and/or steps described that the applications designer will selectively decide, depending upon the practical considerations of the particular implementation, to carry out and/or locate within the jurisdiction of the USA. For example, any of the foregoing described method steps and/or system components which may be performed remotely over a network (e.g., without limitation, a remotely located server) may be performed and/or located outside of the jurisdiction of the USA while the remaining method steps and/or system components (e.g., without limitation, a locally located client) of the forgoing embodiments are typically required to be located/performed in the USA for practical considerations. In client-server architectures, a remotely located server typically generates and transmits required information to a US based client, for use according to the teachings of the present invention. Depending upon the needs of the particular application, it will be readily apparent to those skilled in the art, in light of the teachings of the present invention, which aspects of the present invention can or should be located locally and which can or should be located remotely. Thus, for any claims construction of the following claim limitations that are construed under 35 USC § 112 (6)/(f) it is intended that the corresponding means for and/or steps for carrying out the claimed function are the ones that are locally implemented within the jurisdiction of the USA, while the remaining aspect(s) performed or located remotely outside the USA are not intended to be construed under 35 USC § 112 (6) pre-AIA or 35 USC § 112 (f) post AIA. In some embodiments, the methods and/or system components which may be located and/or performed remotely include, without limitation: any one or more of the operations as presented above related to the iterative and/or systematic identification of at least partially related chemical compounds, formulas, structures, and/or the like relative to an input formula.

It is noted that according to USA law, all claims must be set forth as a coherent, cooperating set of limitations that work in functional combination to achieve a useful result as a whole. Accordingly, for any claim having functional limitations interpreted under 35 USC § 112 (6)/(f) where the embodiment in question is implemented as a client-server system with a remote server located outside of the USA, each such recited function is intended to mean the function of combining, in a logical manner, the information of that claim limitation with at least one other limitation of the claim. For example, in client-server systems where certain information claimed under 35 USC § 112 (6)/(f) is/(are) dependent on one or more remote servers located outside the USA, it is intended that each such recited function under 35 USC § 112 (6)/(f) is to be interpreted as the function of the local system receiving the remotely generated information required by a locally implemented claim limitation, wherein the structures and or steps which enable, and breathe life into the expression of such functions claimed under 35 USC § 112 (6)/(f) are the corresponding steps and/or means located within the jurisdiction of the USA that receive and deliver that information to the client (e.g., without limitation, client-side processing and transmission networks in the USA). When this application is prosecuted or patented under a jurisdiction other than the USA, then "USA" in the foregoing should be replaced with the pertinent country or countries or legal organization(s) having enforceable patent infringement jurisdiction over the present patent application, and "35 USC § 112 (6)/(f)" should be replaced with the closest corresponding statute in the patent laws of such pertinent country or countries or legal organization(s).

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" or "steps for" claim limitation implies that the broadest initial search on 35 USC § 112(6) (post AIA 112(f)) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112(6) (post AIA 112(f)) when such corresponding structures are not explicitly disclosed in the foregoing patent specification. Therefore, for any invention element(s)/structure(s) corresponding to functional claim limitation(s), in the below claims interpreted under 35 USC § 112(6) (post AIA 112(f)), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112(6) (post AIA 112(f)) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112(6) (post AIA 112(f)), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing novel computational and/or combinatorial computer-implemented algorithmic search techniques for chemical structures, moieties, formulas and/or the like for in-silico, e.g., performed via computer simulation in reference to biological or biochemical experiments, etc., lead generation according to the present invention will be apparent to those skilled in the art. Various aspects of the invention have been described above by way of illustration, and the specific embodiments disclosed are not intended to limit the invention to the particular forms disclosed. The particular implementation of the novel computational and/or combinatorial computer-implemented algorithmic search techniques may vary depending upon the particular context or application. By way of example, and not limitation, the novel computational and/or combinatorial computer-implemented algorithmic search techniques described in the foregoing were principally directed to chemical, biological, biochemical and related implementations; however, similar techniques may instead be applied to the field of genetics, physics, quantum theory and/or the like, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

Only those claims which employ the words "means for" or "steps for" are to be interpreted under 35 USC 112, sixth paragraph (pre AIA) or 35 USC 112(f) post-AIA. Otherwise, no limitations from the specification are to be read into any claims, unless those limitations are expressly included in the claims.

What is claimed is:

1. A non-transitory computer-readable storage medium with an executable program stored thereon, wherein the program instructs one or more processors to perform a method comprising:

steps for inputting a formula to search for;

steps for inputting a list of valences required for each atom;

steps for inputting a list of atoms comprising the space to search;

steps for calculating an index of the input formula, a constant number index step;

steps for enumerating all sums which add to precisely a constant number corresponding to the result of employing a partition algorithm based upon certain atomic numbers and said constant number index step;

steps for determining the quantity of a first atom;

steps for Sub-enumerating to choose the other atoms wherein said Sub-enumerating steps recursively calls itself;

steps for branch testing iform in said Sub-enumerate steps, which defers H quantity to last;

steps for calculating an H quantity in Isomer with a maximum hydrogen;

steps for interpreting a formula as all non-fragment isomers of said formula, wherein bonds between two atoms are either single, double or triple, and Isomers with rings are allowed as well as non-cyclic isomers and isomers of any topology, and wherein a canonical isomer comprises a maximum number of H or valence 1 atoms;

steps for configuring atoms in a line with highest valence atoms at both ends, single bonded to form a canonical isomer;

steps for adding a double bond, triple bond or ring will reduce number of H by an even number;

steps for branch testing maximum h, which compares canonical isomer to a putative partition, wherein if test false leaves odd number of H all isomers of this kind are optionally simultaneously be rejected, and if test true prints the formula with numbers of each atom specified;

steps for calculating a maximum hydrogen number, wherein the first branch skips H itself and any omitted atoms, and wherein said maximum hydrogen number steps loops over other atoms to find maximum valence, incrementing said maximum hydrogen number in the loop, except valence 1 are decremented;

steps for calculating a second highest valence, in which branches test if there is a solitary atom then determines that N has the second highest valence, and in which a branch on i skips H and any omitted atoms once again; and steps for generating a final chemical structure, moieties, formulas and/or the like for in-silico, and communicating it to a computer simulation to carry out biological or biochemical experiments a means for lead generation.

2. The method of claim 1 further comprising the steps for creating a composition by computer simulation and/or robotic biological or biochemical experiments at least partially based upon employing, as lead compound(s), the final chemical structure, moieties, and/or formula(s) generated and communicated.

3. The method of claim 2, further comprising the steps for presenting the periodic table up to atomic number 48, being 24 spin up and 24 spin down.

4. A non-transitory computer-readable storage medium with an executable program stored thereon, wherein the program instructs one or more processors to perform a method comprising steps for:

calculating an index of an input formula(s), a constant number index step;

determining the quantity of a first atom;

calculating an H quantity in Isomer with a maximum hydrogen number;

interpreting said formula as all non-fragment isomers of said formula;

reducing number of H by an even number by way of configuring atoms in a line with highest valence atoms at both ends, and/or single bonded to form a canonical isomer;

adding a double bond, triple bond or ring to reduce said number of H by an even number;

calculating a maximum hydrogen number;

calculating a second highest valence;

generating a final list of lead compound(s), said final list of lead compound(s) comprise of chemical structure(s), structure(s), moieties(s), and/or formula(s) for in-silico; and outputting said final list of lead compound(s), said outputted lead compound(s) final list being suitable and operable for communication directly to an external computer simulation program product that intakes said final lead compound(s) list as a focused and optimal starting point for conducting at least one of a biological, a biochemical and simulation experiments towards discovering a new and useful and desirable chemical compound not previously known.

5. The method of claim 4, further comprising the steps for allowing bonds between two atoms that are either single, double or triple, and Isomers with rings as well as non-cyclic isomers and isomers of any topology.

6. The method of claim 5, wherein a canonical isomer comprises a maximum number of H or valence 1 atoms.

* * * * *